(12) United States Patent
Gorczynski et al.

(10) Patent No.: US 7,291,330 B2
(45) Date of Patent: Nov. 6, 2007

(54) MD-1 INHIBITORS AS IMMUNE SUPPRESSANTS

(75) Inventors: Reginald M. Gorczynski, Willowdale (CA); David A. Clark, Burlington (CA)

(73) Assignee: Trillium Therapeutics Inc., Toronto, Ontario (CA)

( * ) Notice: Subject to any disclaimer, the term of this patent is extended or adjusted under 35 U.S.C. 154(b) by 629 days.

(21) Appl. No.: 10/221,154

(22) PCT Filed: Mar. 16, 2001

(86) PCT No.: PCT/CA01/00346

§ 371 (c)(1),
(2), (4) Date: Jan. 8, 2003

(87) PCT Pub. No.: WO01/68697

PCT Pub. Date: Sep. 20, 2001

(65) Prior Publication Data

US 2004/0018972 A1    Jan. 29, 2004

Related U.S. Application Data

(60) Provisional application No. 60/189,986, filed on Mar. 17, 2000.

(51) Int. Cl.
*A61K 39/395* (2006.01)
*C07K 16/00* (2006.01)
*C07K 16/28* (2006.01)

(52) U.S. Cl. .............................. 424/130.1; 530/387.1; 530/387.9; 424/172.1; 424/173.1

(58) Field of Classification Search .................. None
See application file for complete search history.

(56) References Cited

U.S. PATENT DOCUMENTS

2006/0094006 A1* 5/2006 Franchini et al. ............. 435/6

FOREIGN PATENT DOCUMENTS

WO    WO99/24565    5/1999

OTHER PUBLICATIONS

Begum et al. (1999) Biochem. Biophys. Res. Comm. 256:325-329.*
Chan et al., J. Exp. Med., 1998, 188:93-101.*
Newell et al., Transplantation, 2006, 81: 1-6.*
Huang Z, Pharmacol. Ther., 2000, 86: 201-215.*
Gorczynski, R. et al., "Regulation of Gene Expression of Murine MD-1 Regulates Subsequent T Cell Activation and Cytokine Production". J. of Immunology, vol. 165, No. 4, p. 1925-1932(2000).
Begum, N.A. et al. "Human MD-1 Homologue is a BCG-Regulated Gene Product in Monocytes: Its Identification by Differential Display". Biochem. & Biophy. Research Communications, vol. 256, p. 325-329 (1999).
Miura, Y. et al. "RP105 is Associated with MD-1 and Transmits an Activation Signal in Human B Cells". Blood, vol. 92, No. 8 p. 2815-2822 (1998).
Miyake, K. et al. "Mouse MD-1, a Molecule that is Physically Associated with RP105 and Positively Regulates Its Expression". J. of Immunology, The Williams & Wilkins Co., vol. 161, p. 1348-1353, (1998).

* cited by examiner

*Primary Examiner*—Phillip Gambel
*Assistant Examiner*—Ilia Ouspenski
(74) *Attorney, Agent, or Firm*—Bereskin & Parr; Micheline Gravelle

(57) ABSTRACT

Methods and compositions for inducing immune suppression are disclosed. The methods involve administering an effective amount of an agent that inhibits MD-1 with or without an OX-2 protein or a nucleic acid encoding an OX-2 protein. The methods are useful in preventing graft rejection, fetal loss, autoimmune disease, and allergies. Methods and compositions for preventing immune suppression are also disclosed. The methods involve administering an effective amount of MD-1 or an agent that activates or stimulates MD-1.

3 Claims, 15 Drawing Sheets

Effect of in vivo treatment of renal transplanted mice with anti-MD-1 reagents on cytokines and MD-1 expression S= control sense probe; AS=anti-sense probe (digoxigenin-tagged); OX-2 = CD200; e=embryo; t= trophoblast; d=decidua; l= residual uterine lumen; m= mesometrial pole, site of accumulation of granulated lymphoid cells forming 'metrial gland'.

"Predicted" curves based on pharmacologic drug response curves; single hit curve typical of cytotoxic T cell (Ctl)-target lysis.

* P< 0.05 compared to control curve. Normal rabbit serum Ig has no effect on cytokine-dependent abortion rates (2,20).

MD-1 INHIBITORS AS IMMUNE SUPPRESSANTS

FIELD OF THE INVENTION

The invention relates to methods and compositions for immunoregulation comprising the regulating the gene expression and/or the activity of MD-1.

BACKGROUND OF THE INVENTION

The immune system protects the body from infectious agents and disease and is critical to our survival. However, in certain instances, the immune system can be the cause of illness. One example is in autoimmune disease wherein the immune system attacks its own host tissues, in many instances causing debilitating illness and sometimes resulting in death. Examples of autoimmune diseases include multiple sclerosis, type 1 insulin-dependent diabetes mellitus, lupus erythematosus and arthritis. A second example where the immune system can cause illness is during tissue or organ transplantation. Except in the cases of genetically identical animals, such as monozygotic twins, tissue and organ transplants are rejected by the recipient's immune system as foreign. The immune reaction against transplants is even more pronounced in transplantation across species or xenotransplantation. A third example where the immune system harms the host is during an allergic reaction where the immune system is activated by a generally innocuous antigen causing inflammation and in some cases tissue damage. Another example where the immune system has a negative effect is in fetal loss or spontaneous abortions wherein the maternal immune system rejects the fetas as being foreign In order to inhibit the detrimental immune reactions during transplantation, autoimmune disease and allergic reactions, immunosuppressive drugs (such as cyclosporin A, tacrolimus, and corticosteroids) or antibody therapies (such as anti-T cell antibodies) are generally administered. Unfortunately, these non-specific modes of immunosuppression generally have undesirable side effects. For example, cyclosporin may cause decreased renal function, hypertension, toxicity and it must be administered for the life of the patient. Corticosteroids may cause decreased resistance to infection, painful arthritis, osteoporosis and cataracts. The anti-T cell antibodies may cause fever, hypertension, diarrhea or sterile meningitis and are quite expensive.

In view of the problems associated with immunosuppression, there has been an interest in developing methods or therapies that induce unresponsiveness or tolerance in the host to a transplant, to "self" tissues in autoimmune disease and to harmless antigens associated with allergies. The inventors have been studying the mechanisms involved in transplant rejection and has developed methods for inducing a state of antigen-specific immunological tolerance in transplantation. In particular, in animal allograft models, it has demonstrated that graft survival can been increased if the recipient animal is given a pre-transplant infusion via the portal vein of irradiated spleen cells from the donor animal. In contrast, a pre-transplant infusion via the tail vein does not prolong graft survival where there are multiple antigenic incompatibilities (10,11). Using a DNA subtractive hybridization approach, it was further shown that tolerance in pv immunized mice is associated with increased expression of a number of distinct mRNAs (12). One was shown to encode OX-2, a molecule expressed on the surface of dendritic cells. OX-2 was initially described by Barclay (13), though at the time its function was unknown. Gorczynski et al. subsequently showed that anti-OX-2 monoclonal antibodies blocked the protective effect of pv immunization in mice receiving renal allografts (12) and rats receiving small intestinal transplants (14). Moreover anti-OX-2 blocked the polarization to type-2 cytokine production seen in these models. More recently, the inventors demonstrated that a soluble immunoadhesion, in which the extracellular domain of OX-2 was linked to a murine IgG2aFc region, was itself capable of inhibiting T cell allostimulation and type-1 cytokine production (IL-2, IFNγ) in vitro and in vivo (15). These and other data (16) indicate that OX-2 is a novel "coregulatory" molecule, which controls the outcome of TCR: antigen encounter. The inventors also determined that OX-2 is capable of preventing fetal loss (WO 99/24565). The OX-2 protein has recently been renamed CD200 and both terms may be used interchangeably.

In addition to OX-2 (CD200), the inventors determined that other molecules are differentially expressed following pv immunization. The full length sequence for one of these was determined to be MD-1. MD-1 has been reported to regulate expression of RP105 on B cells (26, 30). RP105, which is also expressed on dendritic cells (18), is a member of a family of molecules bearing a leucine-rich repeat motif which serves an important, and evolutionarily conserved, function in immunity in a number of species (19) This family, which includes the lipopolysaccharide (LPS) receptor CD14 (20), acts as receptors for invariant molecular structures in pathogens which trigger innate immune responses, including the induction of inflammatory cytokines (IL-1, IL-8, IL-6, IFNγ) as well as some costimulatory molecules (e.g. CD80)(21).

Understanding the molecular mechanisms involved in the induction of tolerance may lead to the development of methods of inducing immune suppression that may be useful in transplantation, autoimmune disease, allergies, fetal loss, and other related conditions requiring immune modulation.

SUMMARY OF THE INVENTION

The present inventors have determined that MD-1 is a potent immune modulator. In particular, the present inventors have demonstrated that inhibiting MD-1 prolongs graft survival and inhibits the production of cytotoxic T lymphocytes (CTLs) as well as the cytokines IL-2 and IFNγ. The inventors have further demonstrated that inhibiting MD-1 inhibits cytokine-induced fetal loss. The results demonstrate that MD-1 is an important immune regulatory molecule and can lead to the development of novel therapies for modulating an immune response.

Consequently, broadly stated, the present invention provides a method of modulating an immune response comprising modulating the expression or activity of MD-1.

In one aspect, the present invention provides a method of suppressing an immune response comprising administering an effective amount of an inhibitor of MD-1 to an animal in need of such treatment.

In one embodiment, the present invention provides a method of inducing immune suppression or tolerance to a transplanted organ or tissue in a recipient animal comprising administering an effective amount of an inhibitor of MD-1 to the recipient animal prior to the transplantation of the organ or tissue.

In another embodiment, the present invention provides a method of preventing or inhibiting graft versus host disease in a recipient animal receiving an organ or tissue transplant comprising administering an effective amount of an inhibitor of MD-1 to the organ or tissue prior to the transplantation in the recipient animal.

In yet another embodiment, the present invention provides a method of preventing or inhibiting fetal loss comprising administering an effective amount of an inhibitor of MD-1 to an animal in need thereof.

In a further embodiment, the present invention provides a method of preventing or treating an autoimmune disease comprising administering an effective amount of an inhibitor of MD-1 to an animal having, suspected of having, or susceptible to having an autoimmune disease.

In yet a further embodiment, the present invention provides a method of preventing or treating an allergy comprising administering an effective amount of an inhibitor of MD-1 to an animal having or suspected of having an allergy.

The invention also includes pharmaceutical compositions containing one or more inhibitors of MD-1 for use in inducing tolerance in transplantation, allergy or autoimmune disease or for preventing or treating fetal loss.

In preferred embodiments of the above methods and compositions, the MD-1 inhibitor is an antibody that binds MD-1 or an antisense oligonucleotide that inhibits the expression of MD-1. Also in a preferred embodiment of the invention, the inhibitor of MD-1 is administered in combination with an OX-2 protein or a nucleic acid sequence encoding an OX-2 protein.

As stated above, inhibiting MD-1 can be used to induce immune suppression. Consequently, activating MD-1 may also be useful in preventing immune suppression or inducing an immune response.

Therefore, in another aspect, the present invention provides a method of preventing immune suppression comprising administering an effective amount of an MD-1 protein or a nucleic acid sequence encoding an MD-1 protein to an animal in need thereof.

In one embodiment, the present invention provides a method of inducing fetal loss comprising administering an effective amount of an MD-1 protein or a nucleic acid sequence encoding an MD-1 protein to an animal in need thereof.

The invention also includes pharmaceutical compositions containing an MD-1 protein or a nucleic acid sequence encoding an MD-1 protein for use in inducing or augmenting an immune response. Such compositions can include other molecules that can activate the immune response such as inhibitors of OX-2.

The invention further includes screening assays for identifying substances that modulate MD-1 expression or activity. Such substances may be useful in the therapeutic methods and compositions of the invention.

The invention also includes diagnostic kits and methods for detecting conditions associated with increased, decreased or abnormal expression of MD-1.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which.

DETAILED DESCRIPTION OF THE INVENTION

Figure 1:
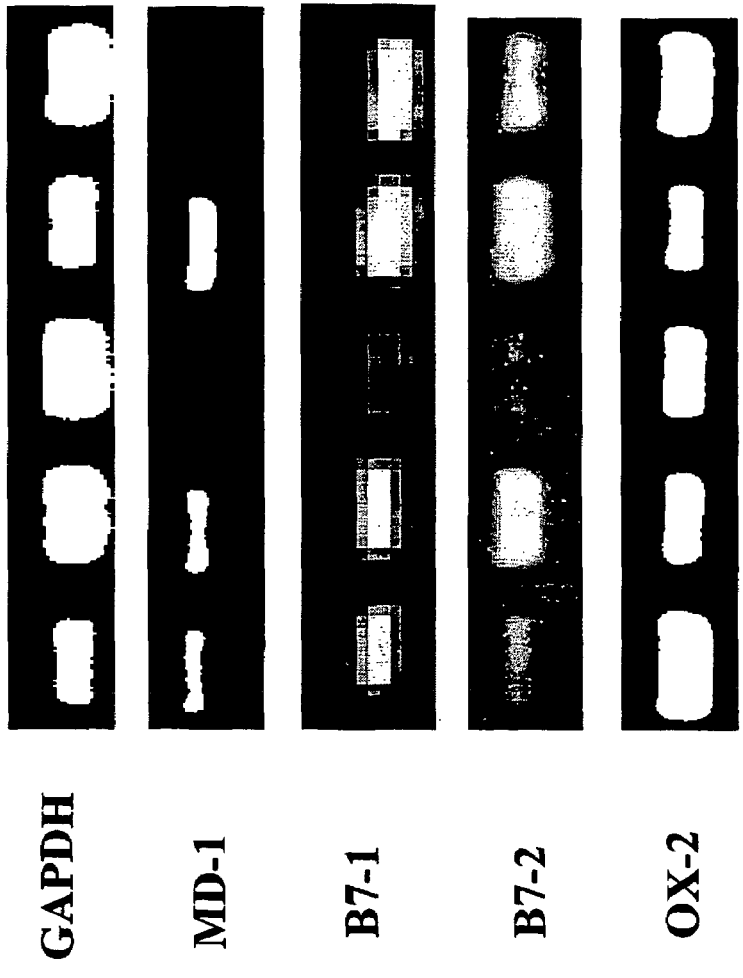
FIG. 1 is a Nothern blot illustrating PCR analysis of the effect of anti-sense oligonucleotides to MD-1 on mRNA of GAPDH, MD-1, B7-1 (CD 80), B7-2 (CD 86) and OX-2. RNA was extracted from bone marrow derived dendritic cells (DC) after overnight LPS stimulation of DC which had been incubated for 6 hr with medium alone, cytofectin, or cytofectin with the ODNs shown. Data show mean (±SD) relative to a medium control GAPDH set as 1.

The inventors have previously shown that the immunoadhesin OX-2 (CD200) comprising the extracellular domain of OX-2 linked to IgG2aFc, inhibits production of IL-2 and IFNγ by activated T cells, increases allograft and xenograft survival in vivo and prevents fetal loss syndrome (see WO 99/24565 to the present inventors which is incorporated herein by reference in its entirety). Since increased expression of OX-2 on dendritic cells (DC) in vivo following pre-immunization via the portal vein is associated with elevated expression of MD-1, the inventors used anti-sense oligodeoxynucleotides (ODNs) to MD-1 to investigate the effect of inhibition of expression of MD-1 by DC on their function in these same assays. The inventors also investigated by FACS analysis, the cell surface expression of OX-2, CD80 and CD86 on DC incubated with ODN-1 blocking MD-1 expression.

The results, described in detail in Examples 1 to 3, demonstrate that blocking MD-1 gene expression inhibits surface expression of CD80 and CD86, but not of OX-2 (CD200). DCs incubated with ODN-1 to MD-1 did not stimulate IL-2 or IFNγ production, but generated cells able to suppress, in a second culture of fresh DC+allogenic T cells, production of IL-2 and IFNγ. This inhibition was blocked by anti-OX-2 mAb. Infusion of DCs pre-incubated with ODN-1 prolonged renal allograft survival, an effect also reversed by anti-OX-2 mAb. The inventors have also shown that antibodies to MD-1 can prolong allograft survival and inhibit CTL and IL-2 production. By FACS, incubation of DC with anti-MD-1 antibody to promote capping eliminated cell surface expression of MD-1 and CD14 without altering DEC205, DC26, CD80, CD86 or OX-2 expression. Thus OX-2 and MD-1 are independent surface molecules on DC which may reciprocally regulate T cell stimulation. MD-1 is linked to CD14, a 'danger receptor complex', and activation of this complex can regulate cell surface expression of CD80/CD86 which signal T cells.

The results, described in detail in Example 4, demonstrate that blocking MD-1 activity inhibits cytokine-induced fetal loss. The results also demonstrate that mRNA for MD-1 is located in the same areas of the pregnant uterus as CD200 and fgl2.

All of the results of the inventors demonstrate that MD-1 is an immune modulating molecule that has utility in a wide range of applications. Accordingly, the present invention includes all uses that relate to the realization of the immune modulatory properties of MD-1 including, but not limited to, the development of therapeutic and diagnostic assays and compositions as well as the preparation and/or isolation of other molecules that modulate MD-1 that may be useful in the therapeutic and diagnostic assays and compositions of the invention.

I. Therapeutic Methods (a) Inducing Immune Suppression

In one aspect, the present invention provides a method of suppressing an immune response comprising administering an effective amount of an inhibitor of MD-1 to an animal in need of such treatment. The invention includes a use of an effective amount of an inhibitor of MD-1 to suppress an immune response or to prepare a medicament to suppress an immune response.

The term "an inhibitor of MD-1" means any molecule or compound that can inhibit the expression of the MD-1 gene or that can inhibit the activity of the MD-1 protein.

In one embodiment, the MD-1 inhibitor is an antisense oligonucleotide that inhibits the expression of MD-1. Antisense oligonucleotides that are complimentary to a nucleic acid sequence from an MD-1 gene can be used in the methods of the present invention to inhibit MD-1. The present inventors have prepared antisense oligonucleotides to MD-1 which are described in Example 1. Preferably the antisense oligonucleotide is ODN-1 having the sequence; 5'AGGGCAGCUGCGACACC3' (SEQ. ID. NO. 1).

Consequently, the present invention provides a method of inducing immune suppression comprising administering an effective amount of an antisense oligonucleotide that is complimentary to a nucleic acid sequence from an MD-1 gene to an animal in need thereof.

The term "antisense oligonucleotide" as used herein means a nucleotide sequence that is complimentary to its target.

The term "oligonucleotide" refers to an oligomer or polymer of nucleotide or nucleoside monomers consisting of naturally occurring bases, sugars, and intersugar (backbone) linkages. The term also includes modified or substituted oligomers comprising non-naturally occurring monomers or portions thereof, which function similarly. Such modified or substituted oligonucleotides may be preferred over naturally occurring forms because of properties such as enhanced cellular uptake, or increased stability in the presence of nucleases. The term also includes chimeric oligonucleotides which contain two or more chemically distinct regions. For example, chimeric oligonucleotides may contain at least one region of modified nucleotides that confer beneficial properties (e.g. increased nuclease resistance, increased uptake into cells), or two or more oligonucleotides of the invention may be joined to form a chimeric oligonucleotide.

The antisense oligonucleotides of the present invention may be ribonucleic or deoxyribonucleic acids and may contain naturally occurring bases including adenine, guanine, cytosine, thymidine and uracil. The oligonucleotides may also contain modified bases such as xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thiolalkyl guanines, 8-hydroxyl guanine and other 8-substituted guanines, other aza and deaza uracils, thymidines, cytosines, ade nines, or guanines, 5-trifluoromethyl uracil and 5-trifluoro cytosine.

Other antisense oligonucleotides of the invention may contain modified phosphorous, oxygen heteroatoms in the phosphate backbone, short chain alkyl or cycloalkyl intersugar linkages or short chain heteroatomic or heterocyclic intersugar linkages. For example, the antisense oligonucleotides may contain phosphorothioates, phosphotriesters, methyl phosphonates, and phosphorodithioates. In an embodiment of the invention there are phosphorothioate bonds links between the four to six 3'-terminus bases. In another embodiment phosphorothioate bonds link all the nucleotides.

The antisense oligonucleotides of the invention may also comprise nucleotide analogs that may be better suited as therapeutic or experimental reagents. An example of an oligonucleotide analogue is a peptide nucleic acid (PNA) wherein the deoxyribose (or ribose) phosphate backbon in the DNA (or RNA), is replaced with a polyamide backbon which is similar to that found in peptides (P. E. Nielsen, et al Science 1991, 254, 1497). PNA analogues have been shown to be resistant to degradation by enzymes and to have extended lives in vivo and in vitro. PNAs also bind stronger to a complimentary DNA sequence due to the lack of charge repulsion between the PNA strand and the DNA strand. Other oligonucleotides may contain nucleotides containing polymer backbones, cyclic backbones, or acyclic backbones. For example, the nucleotides may have morpholino backbone structures (U.S. Pat. No. 5,034,506). Oligonucleotides may also contain groups such as reporter groups, a group for improving the pharmacokinetic properties of an oligonucleotide, or a group for improving the pharmacodynamic properties of an antisense oligonucleotide. Antisense oligonucleotides may also have sugar mimetics.

The antisense nucleic acid molecules may be constructed using chemical synthesis and enzymatic ligation reactions using procedures known in the art. The antisense nucleic acid molecules of the invention or a fragment thereof, may be chemically synthesized using naturally occurring nucleotides or variously modified nucleotides designed to increase the biological stability of the molecules or to increase the physical stability of the duplex formed with mRNA or the native gene e.g. phosphorothioate derivatives and acridine substituted nucleotides. The antisense sequences may be produced biologically using an expression vector introduced into cells in the form of a recombinant plasmid, phagemid or attenuated virus in which antisense sequences are produced under the control of a high efficiency regulatory region, the activity of which may be determined by the cell type into which the vector is introduce In another embodiment, the inhibitor of MD-1 is an MD-1 specific antibody. Antibodies to MD-1 may be prepared as described in Example 2 or using techniques known in the art such as those described by Kohler and Milstein, Nature 256, 495 (1975) and in U.S. Pat. Nos. RE 32,011; 4,902,614; 4,543,439; and 4,411,993, which are incorporated herein by reference. (See also Monoclonal Antibodies, Hybridomas: A New Dimension in Biological Analyses, Plenum Press, Kenneft, McKearn, and Bechtol (eds.), 1980, and Antibodies: A Laboratory Manual, Harlow and Lane (eds.), Cold Spring Harbor Laboratory Press, 1988, which are also incorporated herein by reference). Within the context of the present invention, antibodies are understood to include monoclonal antibodies, polyclonal antibodies, antibody fragments (e.g., Fab, and F(ab')$_2$) and recombinantly produced binding partners.

Administration of an "effective amount" of the inhibitor of MD-1 of the present invention is defined as an amount effective, at dosages and for periods of time necessary to achieve the desired result. The effective amount of the inhibitor of MD-1 of the invention may vary according to factors such as the disease state, age, sex, and weight of the animal. Dosage regima may be adjusted to provide the optimum therapeutic response. For example, several divided doses may be administered daily or the dose may be proportionally reduced as indicated by the exigencies of the therapeutic situation.

The term "animal" as used herein includes all members of the animal kingdom including humans.

The therapeutic methods of the invention can be used to treat any condition wherein it is desirable to modulate MD-1 expression or activity. Such conditions include, but are not limited to, transplantation, autoimmune disease, fetal loss, allergies, inflammatory conditions, septic shock, organ dysfunction, wound healing, neurodegenerative diseases (e.g. Alzheimer's disease), stroke and spinal injury.

In one embodiment, the present invention provides a method of inducing immune tolerance or suppression to a transplanted organ or tissue in a recipient animal comprising administering an effective amount of an inhibitor of MD-1 to the recipient animal prior to the transplantation of the organ or tissue. The invention includes a use of an effective amount of an inhibitor of MD-1 to induce immune tolerance to a transplanted organ or tissue or to prepare a medicament to induce immune tolerance to a transplanted organ or tissue.

The term "inducing immune tolerance" means rendering the immune system unresponsiv to a particular antigen without inducing a prolonged generalized immune deficiency. The term "antigen" means a substance that is capable of inducing an immune response. In th case of autoimmune disease, immune tolerance means rendering the immune system unresponsive to an auto-antigen that the host is recognizing as foreign, thus causing an autoimmune response. In the case of allergy, immune tolerance means rendering the immune system unresponsive to an allergen that generally causes an immune response in the host. In the case of transplantation, immune tolerance means rendering the immune system unresponsive to the antigens on the transplant. An alloantigen refers to an antigen found only in some members of a species, such as blood group antigens. A xenoantigen refers to an antigen that is present in members of one species but not members of another. Correspondingly, an allograft is a graft between members of the same species and a xenograft is a graft between members of a different species.

The recipient can be any member of the animal kingdom including rodents, pigs, cats, dogs, ruminants, non-human primates and preferably humans. The organ or tissue to be transplanted can be from the same species as the recipient (allograft) or can be from another species (xenograft). The tissues or organs can be any tissue or organ including heart, liver, kidney, lung, pancreas, pancreatic islets, brain tissue, cornea, bone, intestine, skin and heamatopoietic cells.

The method of the invention may be used to prevent graft versus host disease wherein the immune cells in the transplant mount an immune attack on the recipient's immune system. This can occur when the tissue to be transplanted contains immune cells such as when bone marrow or lymphoid tissue is transplanted when treating leukemias, aplastic anemias and enzyme or immune deficiencies, for example.

Accordingly, in another embodiment, the present invention provides a method of preventing or inhibiting graft versus host disease in a recipient animal receiving an organ or tissue transplant comprising administering an effective amount of an inhibitor of MD-1 to the organ or tissue prior to the transplantation in the recipient animal. The invention includes a use of an effective amount of an inhibitor of MD-1 to prev nt or inhibit graft versus host disease or to prepare a medicament to prevent or inhibit graft versus host disease.

The present inventors have shown that it is possible to prevent fetal loss by inhibiting the activity of MD-1. Accordingly, the present invention provides a method of preventing or inhibiting fetal loss comprising administering an effective amount of an inhibitor of MD-1 to an animal in need thereof. The invention includes a use of an effective amount of an inhibitor of MD-1 to prevent or inhibit fetal loss or to prepare a medicament to prevent or inhibit fetal loss.

As stated previously, the method of the present invention may also be used to treat or prevent autoimmune disease. In an autoimmune disease, the immune system of the host fails to recognize a particular antigen as "self" and an immune reaction is mounted against the host's tissues expressing the antigen. Normally, the immune system is tolerant to its own host's tissues and autoimmunity can be thought of as a breakdown in the immune tolerance system.

Accordingly, in a further embodiment, the present invention provides a method of preventing or treating an autoimmune disease comprising administering an effective amount of an inhibitor of MD-1 to an animal having, suspected of having, or susceptible to having an autoimmune disease. The invention includes a use of an effective amount of an inhibitor of MD-1 to prevent or inhibit an autoimmune disease or to prepare a medicament to prevent or inhibit an autoimmune disease.

Autoimmune diseases that may be treated or prevented according to the present invention include, but are not limited to, type 1 insulin-dependent diabetes mellitus, adult respiratory distress syndrome, inflammatory bowel disease, dermatitis, meningitis, thrombotic thrombocytopenic purpura, Sjögren's syndrome, encephalitis, uveitic, leukocyte adhesion deficiency, rheumatoid arthritis, rheumatic fever, Reiter's syndrom, psoriatic arthritis, progressive systemic sclerosis, primary biniary cirrhosis, pemphigus, pemphigoid, necrotizing vasculitis, myasthenia gravis, multiple sclerosis, lupus erythematosus, polymyositis, sarcoidosis, granulomatosis, vasculitis, pernicious anemia, CNS inflammatory disorder, antigen-antibody complex mediated diseases, autoimmune haemolytic anemia, Hashimoto's thyroiditis, Graves disease, habitual spontaneous abortions, Reynard's syndrome, glomerulonephritis, dermatomyositis, chronic active hepatitis, celiac disease, autoimmune complications of AIDS, atrophic gastritis, ankylosing spondylitis and Addison's disease.

As stated previously, the method of the present invention may also be used to treat or prevent an allergic reaction. In an allergic reaction, the immune system mounts an attack against a generally harmless, innocuous antigen or allergen. Allergies that may be prevented or treated using the methods of the invention include, but are not limited to, hay fever, asthma, atopic eczema as well as allergies to poison oak and ivy, house dust mites, bee pollen, nuts, shellfish, penicillin and numerous others.

Accordingly, in a further embodiment, the present invention provides a method of preventing or treating an allergy comprising administering an effective amount of an inhibitor of MD-1 to an animal having or suspected of having an allergy. The invention includes a use of an effective amount of an inhibitor of MD-1 to prevent or treat an allergy or to prepare a medicament.

The above described methods for suppressing an immune response using MD-1 inhibitors may be further enhanced by co-administering other immune modulators including but not limited to OX-2, anti-fgl2, anti-B7, anti-CD80 or anti-CD86. Preferably, the MD-1 inhibitors are co-administered with an OX-2 protein or a nucleic acid molecule encoding an OX-2 protein as described in the inventors PCT application no. WO99/24565, which is incorporated herein by reference in its entirety.

(b) Preventing Immune Suppression

In another aspect, the present invention provides a method of preventing immune suppression comprising administering an effective amount of an MD-1 protein or a nucleic acid sequence encoding an MD-1 protein to an animal in need thereof.

The term "MD-1 protein" includes the full length MD-1 protein as well as fragments or portions of the protein. Preferred fragments or portions of the protein are those that are sufficient to induce an immune response or prevent immune suppression. The MD-1 protein or the nucleic acid encoding the MD-1 protein can be readily obtained by one of skill in the art. For example, many MD-1 sequences are available in the GenBank database including the human MD-1 (GenBank Accession No. XM004093 or AF057178) or murine MD-1 (GenBank Accession No. AB007599). In one embodiment the MD-1 protein sequence is human MD-1 (SEQ ID NO: 10) reported in Miura et al., 1998 (30) or mouse MD-1 (SEQ ID NO: 11) also reported in Miura et al. 1998 (30). The MD-1 protein or nucleic acid may be modified from the known sequences to make it more useful in the methods of the present invention.

In one embodiment, the MD-1 protein is prepared as a soluble fusion protein. The fusion protein may contain the extracellular domain of MD-1 linked to an immunoglobulin (Ig) Fc Region. The MD-1 fusion may be prepared using techniques known in the art. Generally, a DNA sequence encoding the extracellular domain of MD-1 is linked to a DNA sequence encoding the Fc of the Ig and expressed in an appropriate expression system where the MD-1-FcIg fusion protein is produced. The MD-1 protein may be obtained from known sources or prepared using recombinant DNA techniques. The protein may have any of the known published sequences for MD-1. For example, the sequences can be obtained from GenBank as described above. The protein may also be modified to contain amino acid substitutions, insertions and/or deletions that do not alter the immunomodulatory properties of the protein. Conserved amino acid substitutions involve replacing one or more amino acids of the MD-1 amino acid sequence with amino acids of similar charge, size, and/or hydrophobicity characteristics. When only conserved substitutions are made the resulting analog should be functionally equivalent to the MD-1 protein. Non-conserved substitutions involve replacing one or more amino acids of the MD-1 amino acid sequence with one or more amino acids which possess dissimilar charge, size, and/or hydrophobicity characteristics.

The MD-1 protein may be modified to make it more therapeutically effective or suitable. For example, the MD-1 protein may be cyclized as cyclization allows a peptide to assume a more favourable conformation. Cyclization of the MD-1 peptides may be achieved using techniques known in the art. In particular, disulphide bonds may be formed between two appropriately spaced components having free sulfhydryl groups. The bonds may be formed between side chains of amino acids, non-amino acid components or a combination of the two. In addition, the MD-1 protein or peptides of the present invention may be converted into pharmaceutical salts by reacting with inorganic acids including hydrochloric acid, sulphuric acid, hydrobromic acid, phosphoric acid, etc., or organic acids including formic acid, acetic acid, propionic acid, glycolic acid, lactic acid, pyruvic acid, oxalic acid, succinic acid, malic acid, tartaric acid, citric acid, benzoic acid, salicylic acid, benzenesulphonic acid, and tolunesulphonic acids.

Administration of an "effective amount" of the MD-1 protein and nucleic acid of the present invention is defined as an amount effective, at dosages and for periods of time necessary to achieve the desired result. The effective amount of the MD-1 protein or nucleic acid of the invention may vary according to factors such as the disease state, age, sex, and weight of the animal. Dosage regima may be adjusted to provide the optimum therapeutic response. For example, several divided doses may be administered daily or the dose may be proportionally reduced as indicated by the exigencies of the therapeutic situation.

There are a large number of situations whereby it is desirable to prevent immune suppression (or induce the immune system) including, but not limited to, the treatment of infections, cancer and Acquired Immune Deficiency Syndrome. Inducing the immune system by administering MD-1 may also be useful in inducing fetal loss as is shown in Example 4.

In one embodiment, the present invention provides a method of inducing fetal loss comprising administering an effective amount of an MD-1 protein or a nucleic acid sequence encoding an MD-1 protein to an animal in need thereof. The invention also includes a use of an MD-1 protein or a nucleic acid encoding an MD-1 protein to induce fetal loss or to prepare a medicament to induce fetal loss.

II. MD-1 Modulators

The present invention also includes the isolation and/or identification of substances to modulate MD-1 expression or activity. Such substances or MD-1 modulators may be useful in the above described therapeutic methods. Two examples of MD-1 modulators include antibodies and antisense molecules which are described in detail above. Other MD-1 modulators may be identified, for example, using the screening assays described below.

(a) Substances that Bind MD-1

Substances that affect MD-1 activity can be identified based on their ability to bind to MD-1.

Substances which can bind with the MD-1 of the invention may be identified by reacting the MD-1 with a substance which potentially binds to MD-1, and assaying for complexes, for free substance, or for non-complexed MD-1, or for activation of MD-1. In particular, a yeast two hybrid assay system may be used to identify proteins which interact with MD-1 (Fields, S. and Song, O., 1989, Nature, 340:245-247). Systems of analysis which also may be used include ELISA.

Accordingly, the invention provides a method of identifying substances which can bind with MD-1, comprising the steps of:
(a) reacting MD-1 and a test substance, under conditions which allow for formation of a complex between the MD-1 and the test substance, and
(b) assaying for complexes of MD-1 and the test substance, for free substance or for non complexed MD-1, wherein the presence of complexes indicates that the test substance is capable of binding MD-1.

Conditions which permit the formation of substance and MD-1 complexes may be selected having regard to factors such as the nature and amounts of the substance and the protein.

The substance-protein complex, free substance or non-complexed proteins may be isolated by conventional isolation techniques, for example, salting out, chromatography, electrophoresis, gel filtration, fractionation, absorption, polyacrylamide gel electrophoresis, agglutination, or combinations thereof. To facilitate the assay of the components, antibody against MD-1 or the substance, or labelled MD-1, or a labelled substance may be utilized. The antibodies, proteins, or substances may be labelled with a detectable substance as described above.

MD-1, or the substance used in the method of the invention may be insolubilized. For example, MD-1 or substance may be bound to a suitable carrier. Examples of suitable carriers are agarose, cellulose, dextran, Sephadex, Sepharose, carboxymethyl cellulose polystyrene, filter paper, ion-exchange resin, plastic film, plastic tube, glass beads, polyamine-methyl vinyl-ether-maleic acid copolymer, amino acid copolymer, ethylene-maleic acid copolymer, nylon, silk, etc. The carrier may be in the shape of, for example, a tube, test plate, beads, disc, sphere etc.

The insolubilized protein or substance may be prepared by reacting the material with a suitable insoluble carrier using known chemical or physical methods, for example, cyanogen bromide coupling.

The proteins or substance may also be expressed on the surface of a cell in the above assay.

The invention also contemplates assaying for an antagonist or agonist of the action of MD-1.

It will be understood that the agonists and antagonists that can be assayed using the methods of the invention may act on one or more of the binding sites on the protein or substance including agonist binding sites, competitive antagonist binding sites, non-competitive antagonist binding sites or allosteric sites.

The invention also makes it possible to screen for antagonists that inhibit the effects of an agonist of MD-1. Thus, the invention may be used to assay for a substance that competes for the same binding site of MD-1.

(b) Peptide Mimetics

The present invention also includes peptide mimetics of the MD-1 of the invention. For example, a peptide derived from a binding domain of MD-1 will interact directly or indirectly with an associated molecule in such a way as to mimic the native binding domain. Such peptides may include competitive inhibitors, enhancers, peptide mimetics, and the like. All of these peptides as well as molecules substantially homologous, complementary or otherwise functionally or structurally equivalent to these peptides may be used for purposes of the present invention.

"Peptide mimetics" are structures which serve as substitutes for peptides in interactions between molecules (See Morgan et al (1989), Ann. Reports Med. Chem. 24:243-252 for a review). Peptide mimetics include synthetic structures which may or may not contain amino acids and/or peptide bonds but retain the structural and functional features of a peptide, or enhancer or inhibitor of the invention. Peptide mimetics also include peptoids, oligopeptoids (Simon et al (1972) Proc. Natl. Acad, Sci USA 89:9367); and peptide libraries containing peptides of a designed length representing all possible sequences of amino acids corresponding to a peptide of the invention.

Peptide mimetics may be designed based on information obtained by systematic replacement of L-amino acids by D-amino acids, replacement of side chains with groups having different electronic properties, and by systematic replacement of peptide bonds with amide bond replacements. Local conformational constraints can also be introduced to determine conformational requirements for activity of a candidate peptide mimetic. The mimetics may include isosteric amide bonds, or D-amino acids to stabilize or promote reverse turn conformations and to help stabilize the molecule. Cyclic amino acid analogues may be used to constrain amino acid residues to particular conformational states. The mimetics can also include mimics of inhibitor peptide secondary structures. These structures can model the 3-dimensional orientation of amino acid residues into the known secondary conformations of proteins. Peptoids may also be used which are oligomers of N-substituted amino acids and can be used as motifs for the generation of chemically diverse libraries of novel molecules.

Peptides of the invention may also be used to identify lead compounds for drug development. The structure of the peptides described herein can be readily determined by a number of methods such as NMR and X-ray crystallography. A comparison of the structures of peptides similar in sequence, but differing in the biological activities they elicit in target molecules can provide information about the structure-activity relationship of the target. Information obtained from the examination of structure-activity relationships can be used to design either modified peptides, or other small molecules or lead compounds that can be tested for predicted properties as related to the target molecule. The activity of the lead compounds can be evaluated using assays similar to those described herein.

Information about structure-activity relationships may also be obtained from co-crystallization studies. In these studies, a peptide with a desired activity is crystallized in association with a target molecule, and the X-ray structure of the complex is determined. The structure can then be compared to the structure of the target molecule in its native state, and information from such a comparison may be used to design compounds expected to possess.

(c) Drug Screening Methods

In accordance with one embodiment, the invention enables a method for screening candidate compounds for their ability to increase or decrease the activity of a MD-1 protein. The method comprises providing an assay system for assaying MD-1 activity, assaying the activity in the presence or absence of the candidate or test compound and determining whether the compound has increased or decreased MD-1 activity.

Accordingly, the present invention provides a method for identifying a compound that affects MD-1 protein activity or expression comprising:

(a) incubating a test compound with a MD-1 protein or a nucleic acid encoding a MD-1 protein; and
(b) determining an amount of MD-1 protein activity or expression and comparing with a control (i.e. in the absence of the test substance), wherein a change in the MD-1 protein activity or expression as compared to the control indicates that the test compound has an effect on MD-1 protein activity or expression.

In accordance with a further embodiment, the invention enables a method for screening candidate compounds for their ability to increase or decrease expression of a MD-1 protein. The method comprises putting a cell with a candidate compound, wherein the cell includes a regulatory region of a MD-1 gene operably joined to a reporter gene coding region, and detecting a change in expression of the reporter gene.

In one embodiment, the present invention enables culture systems in which cell lines which express the MD-1 gene, and thus MD-1 protein products, are incubated with candidate compounds to test their effects on MD-1 expression. Such culture systems can be used to identify compounds which upregulate or downregulate MD-1 expression or its function, through the interaction with other proteins.

Such compounds can be selected from protein compounds, chemicals and various drugs that are added to the culture medium. After a period of incubation in the presence of a selected test compound(s), the expression of MD-1 can be examined by quantifying the levels of MD-1 mRNA using standard Northern blotting procedure to determine any changes in expression as a result of the test compound. Cell lines transfected with constructs expressing MD-1 can also be used to test the function of compounds developed to modify the protein expression. In addition, transformed cell lines expressing a normal MD-1 protein could be mutagenized by the use of mutagenizing agents to produce an altered phenotype in which the role of mutated MD-1 can be studied in order to study structure/function relationships of the protein products and their physiological effects.

Accordingly, the present invention provides a method for identifying a compound that affects the binding of an MD-1 protein and an MD-1 binding protein comprising:

(a) incubating (i) a test compound; (ii) an MD-1 protein and (iii) an MD-1 binding protein under conditions which permit the binding of MD-1 protein to the MD-1 binding protein; and
(b) assaying for complexes of MD-1 protein and the MD-1 binding protein and comparing to a control (i.e. in the absence of the test substance), wherein a reduction of complexes indicates that the compound has an effect on the binding of the MD-1 protein to an MD-1 binding protein.

All testing for novel drug development is well suited to defined cell culture systems which can be manipulated to express MD-1 and study the result of MD-1 protein modulation. Animal models are also important for testing novel drugs and thus may also be used to identify any potentially useful compound affecting MD-1 expression and activity and thus physiological function.

III. Compositions

The invention also includes pharmaceutical compositions containing substances that inhibit MD-1 inhibitors for use in immune suppression as well as pharmaceutical compositions containing substances that enhance MD-1 for use in preventing immune suppression. Substances that inhibit MD-1 include substances that inhibit MD-1 gene expression as well as substances that inhibit MD-1 activity. Such substances include antisense molecules to MD-1, antibodies to MD-1 as well as other substances or MD-1 antagonists identified using the screening assays described herein.

Substances that enhance MD-1 include substances that enhance MD-1 expression and/or activity. Such substances include nucleic acid molecules encoding MD-1, MD-1 proteins and other substances or MD-1 agonists identified using the screening assays described herein.

Such pharmaceutical compositions can be for intralesional, intravenous, topical, rectal, parenteral, local, inhalant or subcutaneous, intradermal, intramuscular, intrathecal, transperitonal, oral, and intracerebral use. The composition can be in liquid, solid or semisolid form, for example pills, tablets, creams, gelatin capsules, capsules, suppositories, soft gelatin capsules, gels, membranes, tubelets, solutions or suspensions.

The pharmaceutical compositions of the invention can be intended for administration to humans or animals. Dosages to be administered depend on individual needs, on the desired effect and on the chosen route of administration.

The pharmaceutical compositions can be prepared by per se known methods for the preparation of pharmaceutically acceptable compositions which can be administered to patients, and such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985).

On this basis, the pharmaceutical compositions include, albeit not exclusively, the active compound or substance in association with one or more pharmaceutically acceptable vehicles or diluents, and contained in buffered solutions with a suitable pH and iso-osmotic with the physiological fluids. The pharmaceutical compositions may additionally contain other agents such as immunosuppressive drugs or antibodies to enhance immune tolerance or immunostimulatory agents to enhance the immune response.

In one embodiment, the pharmaceutical composition for use in inducing immune tolerance comprises an effective amount of an inhibitor of MD-1 in admixture with a pharmaceutically acceptable diluent or carrier. The MD-1 inhibitor is preferably an antisense oligonucleotide to MD-1 or an antibody that binds to MD-1. The pharmaceutical compositions may also contain other active agents such as other immune modulators including, but not limited to OX-2, fgl2, B7, CD80 or CD86 including antagonists, agonists and modulators thereof. Preferably the compositions further contain an OX-2 protein or a nucleic acid molecule encoding an OX-2 protein.

Pharmaceutical compositions comprising nucleic acid molecules may be directly introduced into cells or tissues in vivo using delivery vehicles such as retroviral vectors, adenoviral vectors and DNA virus vectors. They may also be introduced into cells in vivo using physical techniques such as microinjection and electroporation or chemical methods such as coprecipitation and incorporation of DNA into liposomes. Recombinant molecules may also be delivered in the form of an aerosol or by lavage. The nucleic acid molecules of the invention may also be applied extracellularly such as by direct injection into cells.

In another aspect, the pharmaceutical composition for use in preventing immune suppression comprises an effective amount of an MD-1 protein or a nucleic acid encoding an MD-1 protein in admixture with a pharmaceutically acceptable diluent or carrier. Such compositions may be administered either alone or in combination with other active agents such as OX-2 inhibitors.

IV. Diagnostic Assays

The finding by the present inventors that MD-1 is involved in immune regulation allows the detection of conditions involving an increase or decrease in MD-1 activity or expression resulting in an aberrant or inappropriate immune response. Such conditions include, but are not limited to, habitual fetal loss, autoimmune diseases, allergies, immune deficiency diseases, graft rejection, inflammatory conditions, wound healing, neurodegenerative diseases, stroke, spinal injury and conditions that lead to septic shock and organ dysfunction in critically ill patients.

Accordingly, the present invention provides a method of detecting a condition associated with increased or decreased MD-1 expression or activity (including an absence) comprising assaying a sample for (a) a nucleic acid molecule encoding a MD-1 protein or a fragment thereof or (b) an MD-1 protein or a fragment thereof and comparing the amount of MD-1 nucleic acid or protein detected with a suitable control.

(a) Nucleic Acid Molecules

Nucleotide probes can be prepared based on the sequence of MD-1 for use in the detection of nucleotide sequences encoding MD-1 or fragments thereof in samples, preferably biological samples such as cells, tissues and bodily fluids. The probes can be useful in detecting the presence of a condition associated with MD-1 or monitoring the progress of such a condition. Accordingly, the present invention provides a method for detecting a nucleic acid molecules encoding MD-1 comprising contacting the sample with a nucleotide probe capable of hybridizing with the nucleic acid molecule to form a hybridization product, under conditions which permit the formation of the hybridization product, and assaying for the hybridization product.

A nucleotide probe may be labelled with a detectable substance such as a radioactive label which provides for an adequate signal and has sufficient half-life such as 32P, 3H, 14C or the like. Other detectable substances which may be used include antigens that are recognized by a specific labelled antibody, fluorescent compounds, enzymes, antibodies specific for a labelled antigen, and chemiluminescence. An appropriate label may be selected having regard to the rate of hybridization and binding of the probe to the nucleic acid to be detected and the amount of nucleic acid available for hybridization. Labelled probes may be hybridized to nucleic acids on solid supports such as nitrocellulose filters or nylon membranes as generally described in Sambrook et al, 1989, Molecular Cloning, A Laboratory Manual (2nd ed.). The nucleotide probes may be used to detect genes, preferably in human cells, that hybridize to the nucleic acid molecule of the present invention preferably, nucleic acid molecules which hybridize to the nucleic acid molecule encoding MD-1 under stringent hybridization conditions as described herein.

Nucleic acid molecules encoding a MD-1 protein can be selectively amplified in a sample using the polymerase chain reaction (PCR) methods and cDNA or genomic DNA. It is possible to design synthetic oligonucleotide primers from the nucleotide sequence of MD-1 for use in PCR. A nucleic acid can be amplified from cDNA or genomic DNA using oligonucleotide primers and standard PCR amplification techniques. The amplified nucleic acid can be cloned into an appropriate vector and characterized by DNA sequence analysis. cDNA may be prepared from mRNA, by isolating total cellular mRNA by a variety of techniques, for example, by using the guanidinium-thiocyanate extraction procedure of Chirgwin et al., Biochemistry, 18, 5294-5299 (1979). cDNA is then synthesized from the mRNA using reverse transcriptase (for example, Moloney MLV reverse transcriptase available from Gibco/BRL, Bethesda, Md., or AMV reverse transcriptase available from Seikagaku America, Inc., St. Petersburg, Fla.).

(b) Proteins

The MD-1 protein may be detected in a sample using antibodies that bind to the protein as described in detail above. Accordingly, the present invention provides a method for detecting a MD-1 protein comprising contacting the sample with an antibody that binds to MD-1 which is capable of being detected after it becomes bound to the MD-1 in the sample.

Antibodies specifically reactive with MD-1, or derivatives thereof, such as enzyme conjugates or labeled derivatives, may be used to detect MD-1 in various biological materials, for example they may be used in any known immunoassays which rely on the binding interaction between an antigenic determinant of MD-1, and the antibodies. Examples of such assays are radioimmunoassays, enzyme immunoassays (e.g. ELISA), immunofluorescence, immunoprecipitation, latex agglutination, hemagglutination and histochemical tests. Thus, the antibodies may be used to detect and quantify MD-1 in a sample in order to determine its role in particular cellular events or pathological states, and to diagnose and treat such pathological states.

In particular, the antibodies of the invention may be used in immuno-histochemical analyses, for example, at the cellular and sub-subcellular level, to detect MD-1, to localise it to particular cells and tissues and to specific subcellular locations, and to quantitate the level of expression.

Cytochemical techniques known in the art for localizing antigens using light and electron microscopy may be used to detect MD-1. Generally, an antibody of the invention may be labelled with a detectable substance and MD-1 may be localised in tissue based upon the presence of the detectable substance. Examples of detectabl substances include various enzymes, fluorescent materials, luminescent materials and radioactive materials. Examples of suitable enzymes include horseradish peroxidase, biotin, alkaline phosphatase, b-galactosidase, or acetylcholinesterase; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include radioactive iodine I-125, I-131 or 3-H. Antibodies may also be coupled to electron dense substances, such as ferritin or colloidal gold, which are readily visualised by electron microscopy.

Indirect methods may also be employed in which the primary antigen-antibody reaction is amplified by the introduction of a second antibody, having specificity for the antibody reactive against MD-1. By way of example, if the antibody having specificity against MD-1 is a rabbit IgG antibody, the second antibody may be goat anti-rabbit gamma-globulin labelled with a detectable substance as described herein.

Where a radioactive label is used as a detectable substance, MD-1 may be localized by autoradiography. The results of autoradiography may be quantitated by determining the density of particles in the autoradiographs by various optical methods, or by counting the grains.

The following non-limiting examples are illustrative of the present invention:

EXAMPLES

Example 1

Materials and Methors

Mice: Male C3H/HeJ, BALB/c and C57Bl/6 mice were purchased from the Jackson laboratories, Bar Harbour, Maine. Mice were housed 5/cage and allowed food and water ad libitum. All mice were used at 8-12 weeks of age. Fischer 344 (Fi) rats purchased from Sprague Dawley were used for immunization to produce monoclonal anti-MD-1 antibodies.

Monoclonal antibodies and cytokine: The following monoclonal antibodies (Mabs) were obtained from Pharmingen (San Diego, Calif., USA): anti-IL-10 (JES5-2A5; biotinylated, SXC-1), anti-IL-2 (S4B6, ATCC), anti-IL-4 (11B1, ATCC), anti-IFNγ (R4-6A2, ATCC; biotinylated XMG1.2). FITC anti-CD80, FITC anti-CD86, FITC anti-CD40, and anti-thy 1.2, L3T4 (anti-CD4), anti-Ly2.2 (anti-CD8), rabbit complement, FITC-anti-CD3 and FITC-MAC-1 were obtained from Cedarlane Labs, Hornby, Ontario. DEC205 (anti-mouse DC), and F(ab')2 rabbit anti-rat IgG FITC conjugate (non-cross reactive with mouse IgG) was obtained from Serotec, Canada. Rat anti-mouse OX-2 (3B6) was purchased from BioSpark Inc., Mississauga, Ontario (22). Strepavidin horse radish peroxidase and recombinant mouse GM-CSF was purchased from Pharmingen (San Diego, Calif.).

Preparation of cells: Single cell spleen suspensions were prepared aseptically from individual mice in each experiment. After centrifugation, the cells were resuspended in a-Minimal Essential Medium supplemented with 2-mercaptoethanol and 10% fetal bovine serum (aF10).

Bone-marrow derived dendritic cells (DC) were obtained by culture of bone marrow cells in vitro (23). Bone marrow cells were pooled from 3 donors, treated with the mixture of antibodies (L3T4, anti-thyl12, anti-Ly2.2) and rabbit complement, and $2\times10^7$ cells were cultured in 10 ml aF10 in tissue culture flasks with 500 U ml-1 recombinant murine GM-CSF (Pharmingen, USA). Fresh GM-CSF was added every 36 hrs. Cells were separated over lymphopaque on days 3.5 and 7 of culture, and recultured in aF10 with recombinant GM-CSF. An aliquot of the cells was stained at 10 days with DEC205 and FITC anti-rat IgG, or as control, with FITC-anti-CD3. Staining with these antibodies averaged 96%±6% and <4% respectively. The remaining cells were washed, counted and used as described below.

Stimulation with LPS (from B. Abortus—a kind gift from Dr. C. Galanos, Max-Planck Institute for Immunobiology, Freiburg, Germany), was performed for 18 hrs (see text), using LPS at a concentration of 250 ng/ml.

Portal Vein (pv) Immunization was Performed as Described Earlier (24):

The mice were anaesthetized with nembutal, and 1×10⁷ of the cultured allogeneic DC wer injected in 0.1 ml through a superior mesenteric vein using a 30-gauge needle. After injection the needle was rapidly withdrawn and hemostasis secured by gentle pressure with 2 mm³ gel-foam. Complications (hemorrhage post-injection) were seen in fewer than 10% of mice, and these were excluded from analysis.

Renal Transplantation:

This procedure was performed as described elsewhere (11). In brief, one kidney was removed and replaced with the donor kidney, with the remaining host kidney excised 2 days later. All renal transplant recipients received im injection with cefotetan (30 mg/Kg) on the day of transplantation and for 2 succeeding days. All animals received im cyclosporin A (15 mg/Kg) daily for the first 2 days post transplant. Pre-treatment of recipients with DC immunization was as described in individual studies. Where animals received in addition, treatment with monoclonal antibody 3B6 following transplantation, 5 sequential iv injections of 100 mg Ig in 300 ml saline were given 36 hrs apart, beginning at the day of transplantation. Control animals received equivalent injections of a control Ig (from pooled normal rat serum).

Cytotoxicity and Cytokine Assays:

To assess induction of cytotoxic T lymphocytes (CTL) and/or cytokine production, C3H/HeJ responder cells were stimulated with an equal number of mitomycin-C-treated (45 min at 37° C.) allogeneic or control spleen stimulator cells in triplicate cultures in αF10. Supernatants were pooled at 40 hr from replicate wells and each was assayed in triplicate in ELISA assays for cytokine production as described below. In some experiments, the cultures were continued to 72 hrs and received 1 mCi/well of 3HTdR; proliferation was measured by harvesting the contents of the well 14 hr later and counting in a well-type b-counter. When cytotoxicity was measured, the cultures were continued to day 5 when the cells were harvested and pooled from replicate wells, counted, and cultured at various effector: target ratios with $^{51}$Cr 72 hr spleen ConA blasts as target cells. Supernatants were sampled at 4 hrs for determination of % specific $^{51}$Cr release.

IL-2 and IL-4 activity were assayed by bioassay using the IL-2- or IL-4-depend nt cell lines, CTLL-2 and CT4.S respectively. Recombinant cytokines for standardization of assays was purchased from Genzyme (Cambridge, Mass.). IL-2 assays were set up in the presence of 11B11 antibody to block potential stimulation of CTLL-2 by IL-4; IL-4 assays were set up in the presence of S4B6 antibody to block IL-2 mediated stimulation. Both the IL-2 and IL-4 assays reproducibly detected 20 pg of recombinant cytokine added to cultures. The concentration of mAbs used blocked 50 ng of cytokine activity. IFNγ and IL-10 were assayed using ELISA assays. For IFNγ, the assay used flat-bottomed 96-well NUNC plates (Gibco, BRL) coated with 100 ng ml-1 R4-6A2. Varying volumes of supernatant were bound in triplicate at 4° C., washed ×3, and biotinylated anti-IFNγ (XMG1.2) was added. After washing, the plates were incubated with streptavidin-horse radish peroxidase (Cedarlane Labs), developed with appropriate substrate, and OD405 determined using an ELISA plate reader. Recombinant IFN-γ for standardization was obtained from Pharmingen (U.S.A.). IL-10 was assayed using a similar ELISA system with JES5-2A5 as the capture antibody, and biotinylated SXC-1 as developing antibody. Recombinant IL-10 for standardization of this assay was obtained from Pepro Tech Inc. (Rocky Hill, N.J.). Each assay reliably detected the relevant cytokine at levels in the range 40 to 4000 pg ml-1.

Antigen Preparation, Immunization and Production of mAb to MD-1:

Details on the preparation and characterization of these reagents is given elsewhere (see Example 2). In brief, 2 Fisher rats were immunized by ip injections of 200 μg of KLH-coupled peptide (representing an exposed epitope for the predicted amino acid sequence of MD-1 as determined by hydrophobicity plots). Following boosting, spleen cells were harvested, pooled and used for fusion with YB2/0 parental myeloma cells as previously described (25). One-step selection and cloning of the hybridomas was performed in 0.8% methylcellulose medium (Immuno-Precise Antibodies Ltd., Victoria, BC), as described in detail elsewhere (22). Clones were picked and resuspended in wells of 96-well tissue culture plates in 200 μl of aMEM medium containing 1% hypoxanthine/thymidine, 20% fetal bovine serum, 1% OPI, and 1×10⁶ ml-1 BALB/c thymocytes, and culture supernatants screened by FACS for detection of MD-1 as described elsewhere, using CHO cells transduced to express murine MD-1 (see also (22)). The mAb SH1.2.47 described below detected a molecule in extracts of DC with molecular size of 27-30 Kd (the reported size of murine MD-1 is 28 Kda (26)), and stained CHO cells transduced with adenoviral vectors engineered to contain a single copy of MD-1 cDNA, as per published sequence, inserted into the not 1/bamH1 sites. Control CHO cells were transduced with vector containing no MD-1 construct, and showed only background staining. FITC anti-rat IgG was used as secondary antibody.

Preparation and testing of anti-sense oligodeoxynucleotides for MD-1: A series of antisense oligodeoxynucleotides (ODN) to MD-1 were prepared by Midland Reagent Co., Midland, Tex., USA, as described (27), using phosphorothioate modification to produce nuclease resistant material. After preliminary testing to delineate active compounds, the final ODNs used were prepared using further C-5 propynyl modification of pyrimidines in the phosphorothioate starting material (28). Delivery of ODNs to test DC in culture used the cationic lipid GS2888 cytofectin (28). Following 6 hr of incubation in serum and antibiotic free αMEM, the cells were incubated overnight in αF10 with 250 ng ml-1 LPS. Then, the cells were washed exhaustively (–4) with αF10 and used in the assays described. The sequence of the ODNs used was as follows:

```
ODN-1  5'AGGGCAGCUGCGACACC3'   (SEQ.ID.NO.1)

ODN-2  5'CCUGUGGAACAUCAAGU3'   (SEQ.ID.NO.2)

ODN-3  5'AGGGACCUUGGGGUCCC3'   (SEQ.ID.NO.3)
```

Analysis of inhibition of expression of a control gene (GAPDH) and MD-1, OX-2, CD80 and CD86, using ODNs to MD-1, was performed by PCR and Northern analysis in cells transduced with antisense ODNs. FACS analysis using FITC-labeled anti-CD80, anti-CD86, OX-2 and DEC205 mAbs was performed on the ODN-treated cells. In addition, they were used at varying numbers (from 1×10⁴ to 3×10⁵) as stimulator cells (following mitomycin C treatment) for allogeneic C3H/HeJ mouse spleen cells in vitro. Proliferation and induction of CTL or cytokines was assayed as described above.

Statistical analysis: For comparison of DC FACS staining, or cytokine production in different groups assayed in vitro, initial ANOVAs were performed, followed by pair-wise comparison of relevant groups using Student's t-test.

Results

Inhibition of mRNA by ODNs and Surface Expression of MD-1, CD80/CD86, and OX-2:

In the first series of experiments, we asked whether anti-sense ODNs to MD-1 would specifically inhibit DC transcription/translation and surface expression of MD-1 without altering expression of a number of other molecules important in T cell stimulation, such as CD80, CD86, and OX-2. DC were derived from 10-day bone marrow cultures, and transduced with ODNs as described in the Materials and Methods. mRNA expression (assayed by PCR) of GAPDH was used as one control, while in cells tested by FACS analysis, we assessed the expression of DEC205 as a control antigen.

FIG. 1 show results, averaged over 3 studies, where ODN-1 treatment inhibited mRNA expression of MD-1, but not of GAPDH, as assayed by densitometry comparisons of Northern gels, using oligonucleotide probes for the various mRNAs synthesized according to published sequences. There was some inhibition of CD80 (B7-1) and CD86 (B7-2) mRNA, though no perturbation of OX-2 mRNA expression was detectable.

Figure 2:
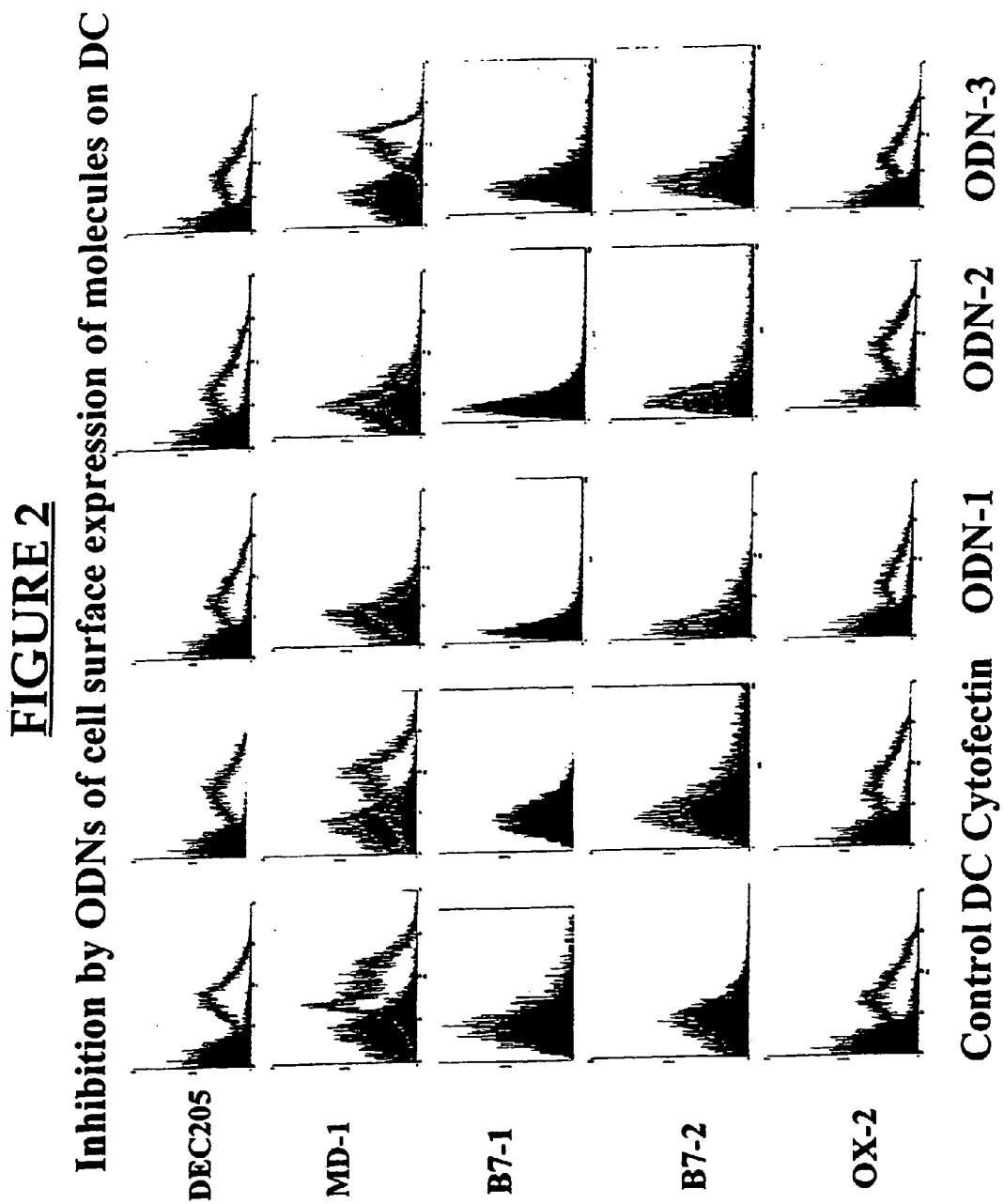
FIG. 2 is FACS analysis of the effect of anti-sense oligonucleotides to MD-1 on cell surface expression of various molecules on dendritic cells (DC). FITC-labeled CD80 and CD86 were used; FITC staining with other mAbs used an indirect reaction with FITC-anti-rat Ig (-staining with FITC anti-rat Ig alone is shown as a solid curve in each of panels a, b and e).

FIG. 2 shows a typical result (from 1 of 6 studies) using FACS analysis. Clear evidence for inhibition of surface expression of MD-1 and CD80 (B7-1), CD86 (B7-2) was seen following treatment with ODNs-1 and -2, but not with ODN-3. No significant inhibition of surface expression of OX-2 or DEC205 was seen by FACS analysis. In all cases no inhibition of any of the transcripts (or cell surface products) tested was seen using ODN-3 (FIGS. 1 and 2).

Figure 3:
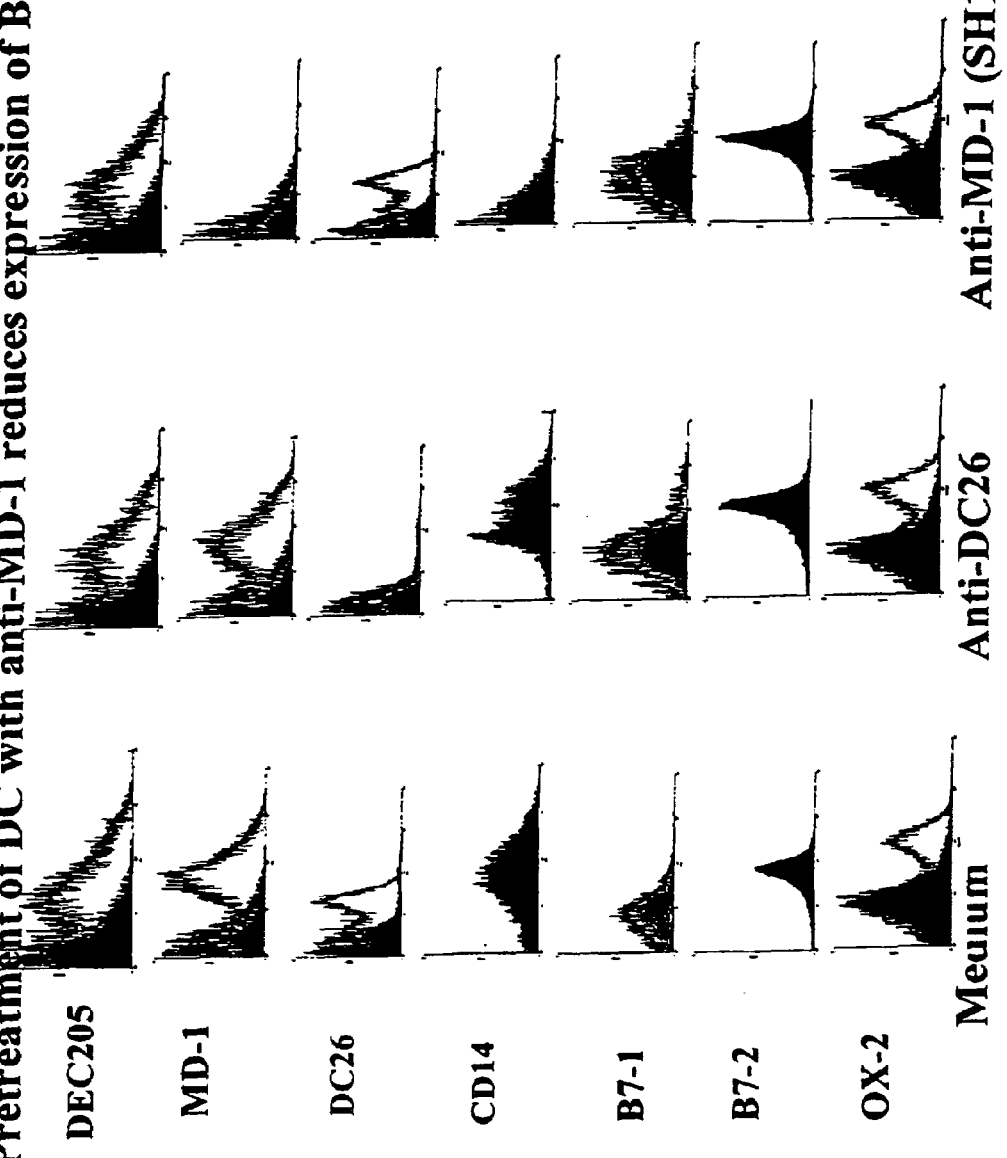
FIG. 3 is FACS analysis of the effect of pretreatment of DC with anti-MD-1 antibody on cell surface expression of molecules on dendritic cells. Cells in the columns shown were preincubated (60 minutes at 4° C.) in medium, rat anti-DC26, or anti-MD-1 (SH1.2.47), prior to washing and incubation at 37° C. with anti-rat Ig. Thereafter cells were stained with different mAbs as in FIG. 2.

A previous report (21) had suggested that MD-1 could regulate cell surface expression of CD80. Indeed, MD-1 controls directly expression of RP105, a molecule with an extracellular leucine-rich-repeat (LRR) sequence, on B cells (26, 30). To investigate MD-1 regulation of CD80/CD86 expression, the inventors preincubated LPS stimulated DC with a rat anti-mouse monoclonal anti-MD-1 antibody (SH1.2.47), or with one of their control rat anti-mouse DC antibodies (DC-26). After incubation at 37° C. for 60 minutes with a goat anti-rat Ig (to patch/cap and internalize cross-linked rat Ig on the cell surface), the DC were fixed with 0.1% glutaraldehyde and stained with FITC conjugated antibodies to CD80, CD86, DEC205, with PE-OX-2, and with anti-MD-1 or anti-DC-26. Control cells were preincubated with the goat anti-rat Ig only prior to incubation with FITC/PE conjugates. Data for one of 3 studies are shown in FIG. 3. It is clear that pre-incubation with anti-MD-1 (or DC-26) mAb abolished subsequent staining of cells with anti-MD-1 (or DC-26). However, staining with conjugated anti-CD80/CD86 mAbs, or with anti-DEC205 or anti-OX-2 was unaffected. Staining with anti-CD14, was reduced by anti-MD-1, in keeping with data elsewhere suggesting molecules of the MD family may be directly associated with CD14 on the cell surface(29). Thus the inhibition of expression of CD80/CD86 with anti-MD-1ODN-1 noted in FIGS. 1 and 2 was not seen when MD-1 was capped directly from the cell surface.

Since it is believed that CD80 and/or CD86, provide an important costimulatory signal for type-1 cytokine production by allostimulated T cells, the inventors next asked whether DC incubated with ODNs to block MD-1, and CD80/CD86 expression would be impaired in this ability. Bone marrow derived DCs of C57Bl/6 origin were incubated with ODNs numbers 1 or 3, cultured overnight with LPS, treated with mitomycin C, and used as stimulator cells for cultures containing allogeneic C3H spleen responder cells. Proliferation and cytokine production in these cultures was assayed. In addition, separate cultures were incubated for 5 days for analysis of CTL. Data for one of four such studies are shown in Table 1.

Incubation of DC with ODN-3 produc d no significant effect on the allo-stimulatory properties of the DC (see first and last rows of Table 1), in keeping with the lack of effect of this anti-sense ODN on expression of costimulatory molecules (see FIGS. 1 and 2). In marked contrast, DC incubated with ODN-1, which inhibits surface expression of MD-1, and CD80/CD86 on the surface after further LPS stimulation of ODN-treated DC (see FIG. 2), were no longer capable of stimulation of CTL, proliferation, or type-1 cytokine production by the allogeneic spleen responder cells (middle row of Table 1). There was a trend to increased production of IL4 and IL-10 in response to ODN-1 treated DC.

DC Incubated with Anti-Sense ODNs for MD-1 Induce "Suppressor Cells" for Type-1 Cytokines:

DC incubated with ODN-1 no longer express CD80/CD86 but expression of OX-2 is preserved (FIG. 2). Since the inventors reported that expression of OX-2 by DC typifies a population of DC capable of inducing cells which can suppress type-1 cytokine production by T cells stimulated with conventional "stimulatory" DC (16), the inventors asked whether cells generated in cultures of spleen cells stimulated with ODN-1-treated (OX-2+) DC were able to suppress an MLR response from freshly stimulated responder T cells. Bone marrow derived C57Bl/6 DC were incubated in the presence of ODN-1 or ODN-3 as above, cultured overnight with LPS, and then used as stimulator cells for normal C3H spleen responder cells for 5 days (3:1 responder:stimulator ratio). Cells were harvested from these cultures, or from control cultures receiving no DC, and added to secondary cultures of fresh C3H spleen responder cells and fresh C57Bl/6 (experimental) or BALB/c (control) bone marrow derived DC. Control (secondary) cultures received only the responder cells and fresh DC. Proliferation, CTL and cytokine production was assayed as before. Data for one of 3 such studies are shown in Table 2.

It is clear from Table 2 that DC pre-treated with ODN-1 and used as stimulator cells in culture do indeed induce a population with antigen-specific suppressive potential as assayed in a second MLR culture; note the failure to inhibit responses stimulated by BALB/c DC. By contrast, cells taken from primary cultures that used untreated DC, or DC treated with ODN-3, had no such suppressive potential.

Role of OX-2 Expression in Suppression of MLR Caused by ODN-1 Treated DC:

To test whether suppression generated by ODN-1 treated DC resulted from the persistent expression of OX-2 by these DC, at the expense of expression of CD80 and CD86, the inventors examined whether the addition of anti-OX-2 mAb to ODN-1-altered DC prevented those cells from inducing the suppression illustrated in Table 2. Data from 1 of 3 such studies are shown in Table 3. It is clear from this Table that anti-OX-2 mAb did indeed block the induction of suppression.

Figure 4:
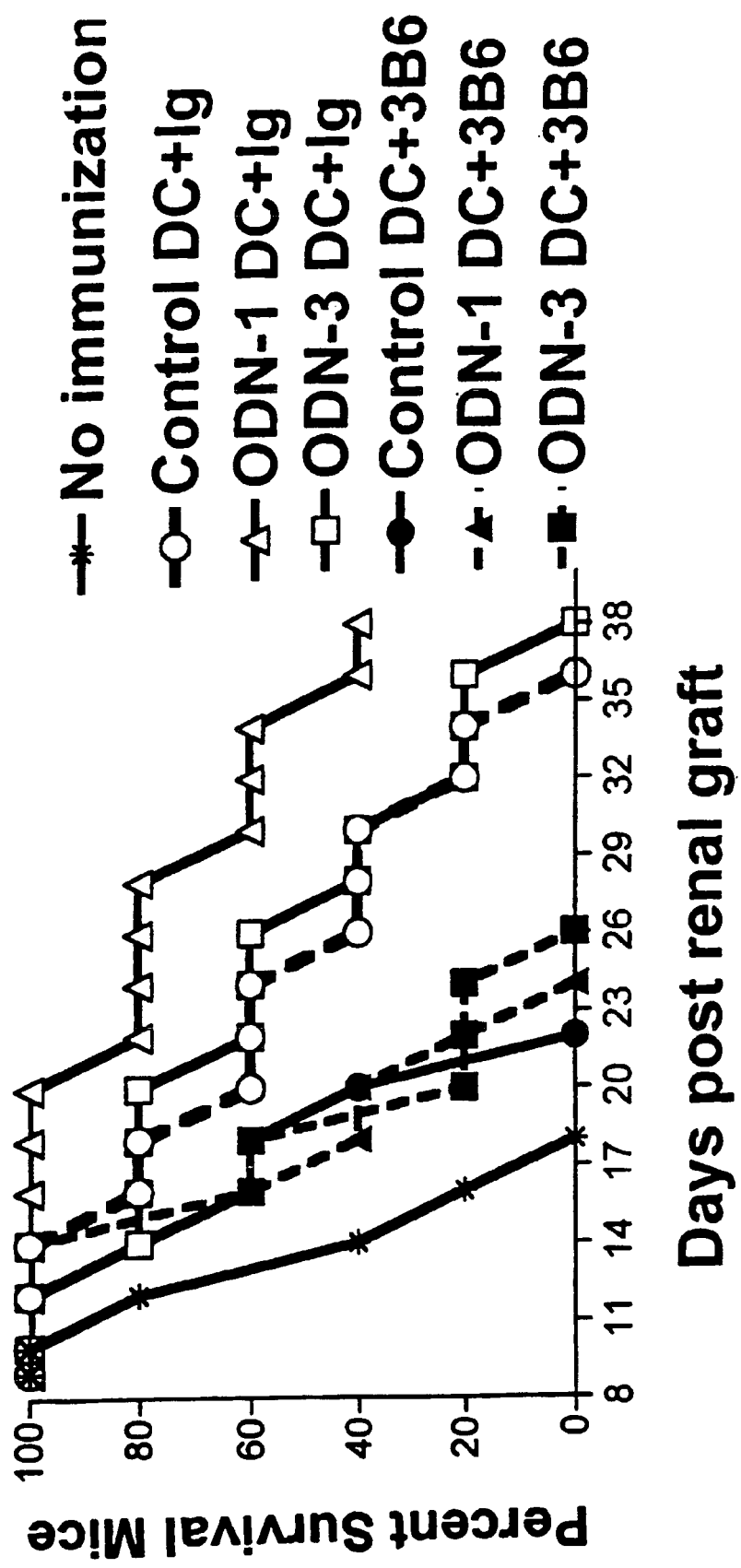
FIG. 4 is a graph showing the synergistic effect of anti-sense oligonucleotides to MD-1 on renal graft survival and the reversal of the effect by anti-OX-2 mAb. Groups of 5 C3H mice received pv immunization with 5×106 C57Bl/6 DC pre-treated for 6 hrs with different ODNs (or with medium only-see FIGS. 1 and 2), followed by C57Bl/6 renal allografts. Mice thereafter were given iv immunizations at 2 day intervals (total of 5 injections) with 100mg anti-OX-2 (3B6) or control normal rat Ig. A control group of transplanted mice received no pv infusion of DC (* in Figure). The group shown as (Δ) in this Figure showed increased survival relative to (○ and □), $p<0.05$; all groups (Δ, ○ and □) showed increased survival relative to the unimmunized control (*), $p<0.05$, Mann-Whitney U-test.

Increased C57Bl/6 Renal Allograft Survival Following pv Infusion of ODN-1-Treated C57Bl/6 DC:

In a final assay, the inventors investigated whether ODN-1 treated DC (with reduced expression of CD80/CD86, but persistent expression of OX-2) would induce prolongation of renal allograft survival after pv immunization, consistent with the proposed role for OX-2 in graft enhancement in vivo (12, 15). C57Bl/6 bone marrow derived DC were incubated with medium alone, or ODN-1 or ODN-3 as before. Cells were further stimulated overnight with LPS, and $5 \times 10^6$ cells infused via the portal vein into groups of C3H/HeJ recipients, which subsequently received C57Bl/6 renal allografts. The mice also received an infusion of control rat Ig, or 3B6 antibody (100 mg/mouse iv at 2 day intervals for a total of 5 injections, beginning on the day of transplant). Survival was monitored daily. Data in FIG. 4 show cumulative data for a total of 6 mice/group.

As expected, pv infusion of bone marrow derived DC led to increased renal allograft survival (○), an effect which was reversed by infusion of anti-OX-2 mAb (●). Interestingly, infusion of ODN-1-treated DC (△), but not ODN-3-treated DC (□), led to a significantly further enhanced graft survival in vivo (p<0.05, Mann Whitney U-test). Further, the increased survival was abolished by infusion of 3B6 mAb (■).

Discussion

The data in this Example show that MD-1 is associated directly with CD14 but not with CD80/CD86, DEC205, or OX-2 on the m mbrane of functional dendritic cells (FIG. 3). However, inhibition of MD-1 synthesis achieved by incubating DC with the oligodeoxynucleotide ODN-1 blocked MD-1 synthesis and indirectly then inhibited up-regulation of the co-stimulatory molecules CD80/CD86 in response to LPS (FIG. 2). These ODN-1-altered DC stimulated Th2-type cytokine production instead of Th1 cytokines when cultured with allogeneic responder splenocytes (Table 1), and proliferation and CTL generation was not seen. Instead, there was generation of cells which could suppress in a secondary test culture the allogeneic response of untreated C3H splenic T cells to unaltered allogeneic DC (Table 2). Generation of these suppressor cells was dependent on persistent OX-2 expression on the ODN-1-treated DC, since anti-OX-2 mAb blocked the effect. The ability of ODN-1-treated DC to enhance allograft survival in vivo via an OX-2-dependent pathway (FIG. 4) supports the view that OX-2 on DC delivers a tolerance signal, whereas MD-1, via indirect up-regulation of CD80/CD86 in response to other inflammatory stimuli (in the experimental case here, from LPS stimulation), delivers an opposing graft rejection stimulus to the recipient.

DC deprived of MD-1 by treatment with ODN-1, and thus of enhanced CD80/CD86 expression following LPS stimulation, had preserved levels of OX-2 and proved particularly effective when injected via the portal vein system in prolonging allograft survival. These data are reminiscent of the synergistic increase in allograft survival the inventors reported when infusion of OX-2+ DC was combined with mAbs to CD80 and CD86 (15). In the current study, ODN-1 is itself contributing to the decrease in functional expression of CD80/CD86 (see FIGS. 1 and 2). Although the inventors did not test the function of DC on which MD-1 had been removed by capping, it would be predicted that such cells would still stimulate the expected Th1 cytokine, proliferative, and CTL responses mediated by CD80/CD86, whose levels remain unperturbed (FIG. 3). To conduct such an experiment, the capped DC would need to be fixed, e.g. with glutaraldehyde, to prevent regeneration of surface MD-1 and CD14.

In these experiments, the inventors have examined surface marker expression and function of bulk populations of DC. It is known that OX-2 is only expressed on a small proportion of DC in bulk bone marrow DC cultures (16). By double staining and flow cytometry, OX-2+ cells are both CD80+ and CD80– (RMG-unpublished). MD-1 expression on these cells has not yet been examined in detail. However, we favour the notion that MD-1+ DC do not express OX-2, since otherwise one might have expected that MD-1-mediated activation signals that up-regulate CD80/CD86 indirectly (FIGS. 1 and 2) would, directly or indirectly, affect OX-2 expression-this was not seen (see FIGS. 1 and 2).

MD-1 and MD-2, which has also now been cloned and characterized (29), appear to be members of a family of molecules. MD-1 was originally reported as a v-myb-regulated gene (26). MD-1 is a secreted molecule, but can be tethered to the cell surface when it is expressed in association with members of a family of molecules expressing an extracellular leucine-rich-repeat (LRR) motif (19). Amongst the latter are, on B cells, RP105, which transmits an activation signal to B cells after cell surface stabilization by MD-1 (17), and members of the Toll-like receptor family, involved in conferring intracellular activation signals following LPS activation, on macrophages/dendritic cells (17, 21, 26). These LRR molecules in general form a family of so-called "pattern recognition receptors", PRRs, and are implicated in signaling for innate immunity following triggering by common conserved motifs on pathogens, i.e. 'danger'. In turn, signaling via LRR-bearing molecules (in association with the MD family of molecules) leads to NF-kB activation and has been reported to be associated with regulation of expression of members of the CD80/CD86 family (21). Thus c-rel knockout mice show decreased B cell activation after cross-linking of RP105 (17). The inventors speculate that infusion of cells into the portal vein represents a stimulus triggering PRRs, with concomitant increased expression of MD-1 which in turn favours increased expression of CD80/CD86. What a PRR might 'see' on allogeneic stimulator cells that signals 'danger' is unknown. Up to the present time, TCR int raction with MHC alloantigen was thought sufficient to lead to a Th1 cytokine/graft rejection response. Now there is evidence of other recognition events important in regulating such responses. The choice of Th1 versus Th2/3 cytokine production by T cells responding to antigen, which has been attributed to an inherent structure of particular MHC-binding peptides may be determined by the recognition by cells of the innate immune system. Specific experiments to test this idea are in progress.

In summary, the data suggest that renal allograft rejection following donor-specific pv immunization is a net result of competing processes, the one (mediated by OX-2) leading to immunosuppression, while the other, regulated by increased expression of MD-1, and thus in turn of CD80/CD86, leads to increased graft rejection. Accordingly, it is proposed that optimal graft survival will result from blocking the latter (e.g. as here, using ODNs to MD-1), and facilitation of the former (e.g. by using OX-2:Fc, or similar immunosuppressive regimes).

Example 2

Preparation and Functional Properties of Polyclonal and Monoclonal Antibodies to Murine MD-1

In this Example, the inventors have characterized a series of heterologous polyclonal sera from rats, hamsters and rabbits, and a rat monoclonal antibody (mAb), from animals immunized with synthetic peptides prepared from MD-1, and shown their specificity for MD-1. Antibodies were screened by ELISA, Western gels, and by FACS, using CHO cells transfected with a cDNA clone encoding murine MD-1. In addition the inventors found that all of these Abs regulate polarization of cytokine production in MLR cultures.

Materials and Methods

Animals 8-week old Lewis rats and Armenian hamsters were obtained from Sprague Dawley farms 8-week old C57BL/6 and C3H male mice were obtained from the Jackson Laboratories, Bar Harbour, Main Selection of Peptide Sequences and Antigen Preparation A hydrophobicity map of murine MD-1 was produced based on the full-length amino acid sequence of the molecule, using DNAsis computer software (Hitachi Software). Two peptide sequences, LVWILTSPSSSDHGS (SEQ. ID. NO. 4) (P1) and SSILNYSYPLCEEDQ (SEQ. ID. NO. 5) (P2), were selected for analysis, each consisting of fifteen amino acid residues expressing the greatest negative hydrophobicity values. P1 and P2 peptides were synthesized by Sigma Genosys, (Texas, USA), coupled to KLH, and used for animal immunization. An aliquot of each peptide was retained for use in ELISA without coupling to KLH.

Immunization and Production of Poly- and Mono-Clonal Abs

New Zealand White rabbits, Lewis rats, and Armenian hamsters were immunized by intraperitoneal injection with 200 μg of either KLH-P1 or KLH-P2 antigen in Complete Freund's Adjuvant. Five subsequent injections were administered at 14-day intervals. Rabbits were test bled (~12 mls/animal) after the fourth immunization and all subsequent sera, including that from the final bleed with sacrifice of recipients, stored at −70° C. until testing. Rats and hamsters received a final immunization 4 days before sacrifice, at which time sera were obtained and spleen cells used for fusion with YB2/0 rat hybridoma parent cells (22,25). Sera or hybridoma supernatants were screened by ELISA for their antibody reactivity with P1- and P2-coated ELISA plates. ELISA-positive hybridomas were re-cloned and examined further by ELISA and FACS, the latter using LPS-stimulated T-depleted splenic cells. N. B. All the ELISA-positive hamster hybridomas initially selected were unstable on longer-term culture, and accordingly no data is shown below for these. The rat hybridoma described below (SH1.2.47) is an IgG2a mAb.

ELISA and FACS analysis of putative MD-1 antibodies

Polystyrene plates (Falcon, N.J., USA) were coated with 50 μl/well of P1 or P2 antigen at a concentration of 4 μg/ml. After binding of antisera or hybridoma supernatants, wells were exhaustively washed and treated with alkaline phosphatase conjugated anti-rabbit, anti-rat or anti-hamster antibodies (Cedarlane, Mississauga, ON, Canada). PNPP (Bio-Rad, Life Science, Hercules, Calif.) was used as substrate and absorbance measured in an automatic ELISA plate reader (TitreTek Multiskan, MCC/340, FlowLabs, Mississauga, ON, Canada).

FACS analysis was performed using the same antibodies and the following cells: 36 hr cultures of LPS-stimulated (1 μg/ml), T-depleted C57BU6 spleen cells (treated with anti-thy1.2 and rabbit complement, both obtained from Cedarlane Labs, Hornby, Ontario), and CHO cells transfected with a cDNA encoding murine MD-1 inserted upstream of the nucleotide sequence for Simian Paramixo Virus antigen, V5, as a "flag epitope" (Invitrogen, Carlsbad, Calif.). Transfection was performed uaing 1-3 μg of LipofectAmine 2000 per 1 μg DNA (Gibco BRL, Burlington, ON, Canada). Cells were screened with anti-V5 mAb, and positive cells further analysed with the putative anti-MD-1 Abs, followed by FITC conjugated anti-rabbit, -rat or -hamster Abs.

Immunoprecipitation and Western Blot Analysis

Putative anti-MD-1 Abs were used in immunoprecipitation with protein A beads (Cedarlane, Mississauga, ON, Canada) and an extract of LPS-stimulated, T-depleted mouse spleen cells (as above) as per the manufacturer's instructions.

The immunoprecipitates, as well as a non-precipitated lysate of LPS-stimulated spleen cells, were electrophoresed in denaturing 12% SDS-PAGE gels, and transferred to nitrocellulose membranes for incubation with Abs. The membranes were subsequently incubated with HRP-conjugated anti-rabbit, -rat or -hamster secondary Abs (Cedarlane, Mississauga, ON, Canada) and developed with ECL substrate (Amersham, Oakville, ON, Canada).

Mixed Leucocyte Reaction (MLR) and Cytokine Production

Allogeneic MLR cultures were set up in the presence or absence of varying concentrations of polyclonal or monoclonal Abs, using a 1:1 mixture of $2.5 \times 10^6$ mitomycin-c treated C57BL/6 stimulator cells and C3H responder spleen cells, in a final volume of 1 ml αMEM medium supplemented with 10% FCS in 24-well culture plates. Culture supernatants were harvested between 1 and 3 days of incubation for analysis of IL-2, IFNγ, IL-4 and IL-10 levels, using an ELISA assay with a commercial set of α-IL-2, α-IFNγ, α-IL4 and α-IL-10 antibodies (Endogene, Mass., USA) as described earlier (12). The calorimetric changes were developed using alkaline phosphatase-streptavidin treatment of the plates followed by addition of PNPP substrate. Based on the OD obtained with recombinant standard cytokines, data were expressed as pg/ml. Cytokine levels plateaued between 36 and 60 hrs post culture initiation, and only data from 2 day cultures is shown below for clarity.

Results

Binding of α-MD-1 Sera and Monoclonal Abs assessed by Western Blotting

Figure 5:
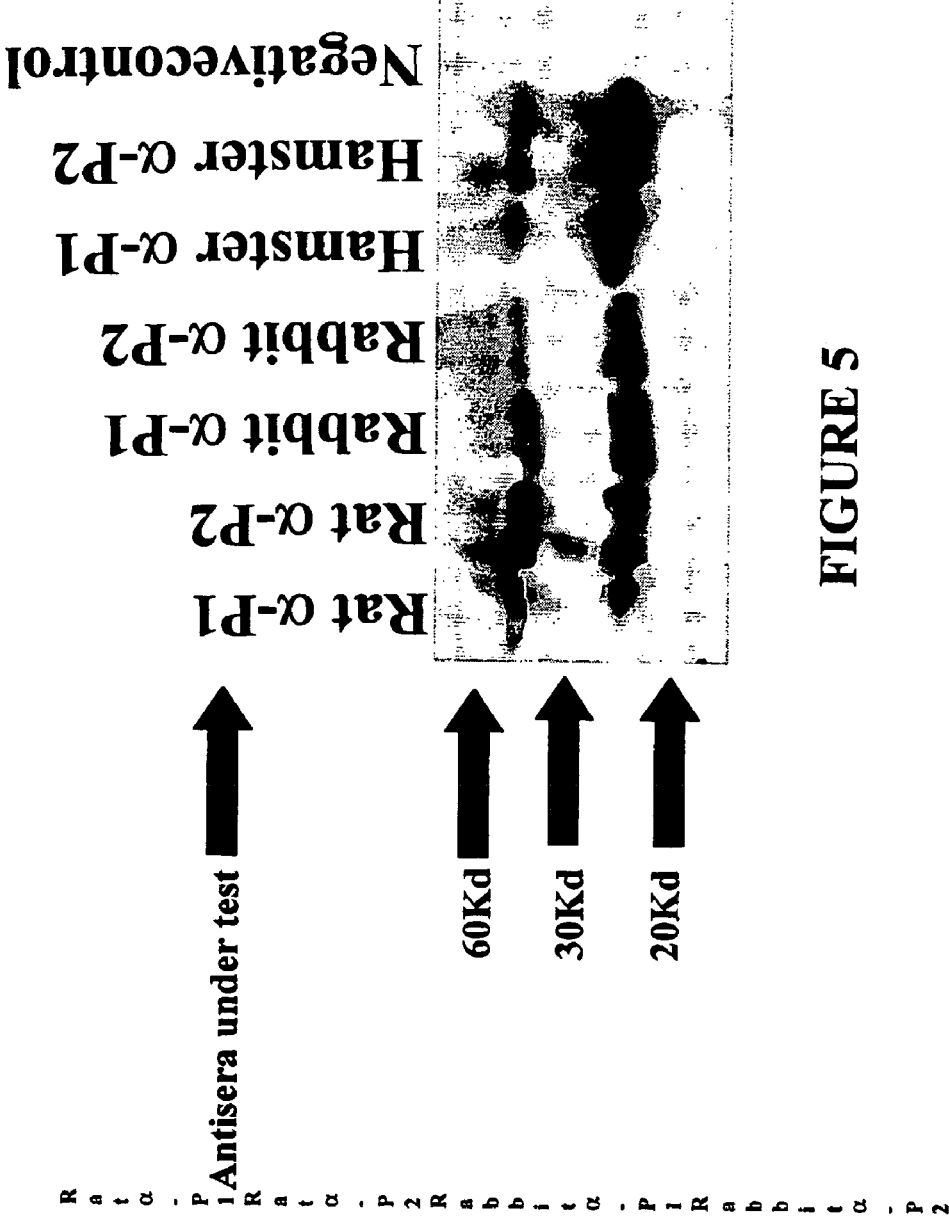
FIG. 5 is a Western Blot showing a 25 kDa molecule recognized by anti-MD-1 antisera. LPS-stimulated mouse spleen cell lysates, pre-cleared with rat, rabbit or hamster pre-immune sera, were precipitated with protein A coated beads and heterologous α-P1 or α-P2 anti-sera produced in rats, rabbits or hamsters respectively. Precipitates were electrophoresed in a denaturing 12% SDS gel and transferred to nitrocellulose membranes before being treated with the putative rat a-MD.1 monoclonal Ab, SH1.2.47. HRP conjugated α-rat Ig was used to facilitate a chemiluminescense reaction that was developed by ECL and visualized on X-ray film.

All polyclonal and monoclonal Abs tested in these experiments were previously screened by ELISA as described in Materials and Methods. As shown in FIG. 5 (data from one of 3 independent studies), all sera precipitated a protein from spleen extracts with molecular weight approximately 25 kDa, which could then be detected by SH1.2.47 mAb. This is consistent with the known molecular weight of the murine MD-1 molecule (29-31). The additional less intense band at ~50 Kd represents cross-reactivity (of the HRP-conjugated anti-rat Ig) with denatured immunoglobulins used for precipitation, and was seen even in gels not developed with the rat mAb (SH1.2.47).

MD-1 Transfected CHO Cells are Stained in FACS by Hetero- and Monoclonal Abs

Figure 6:
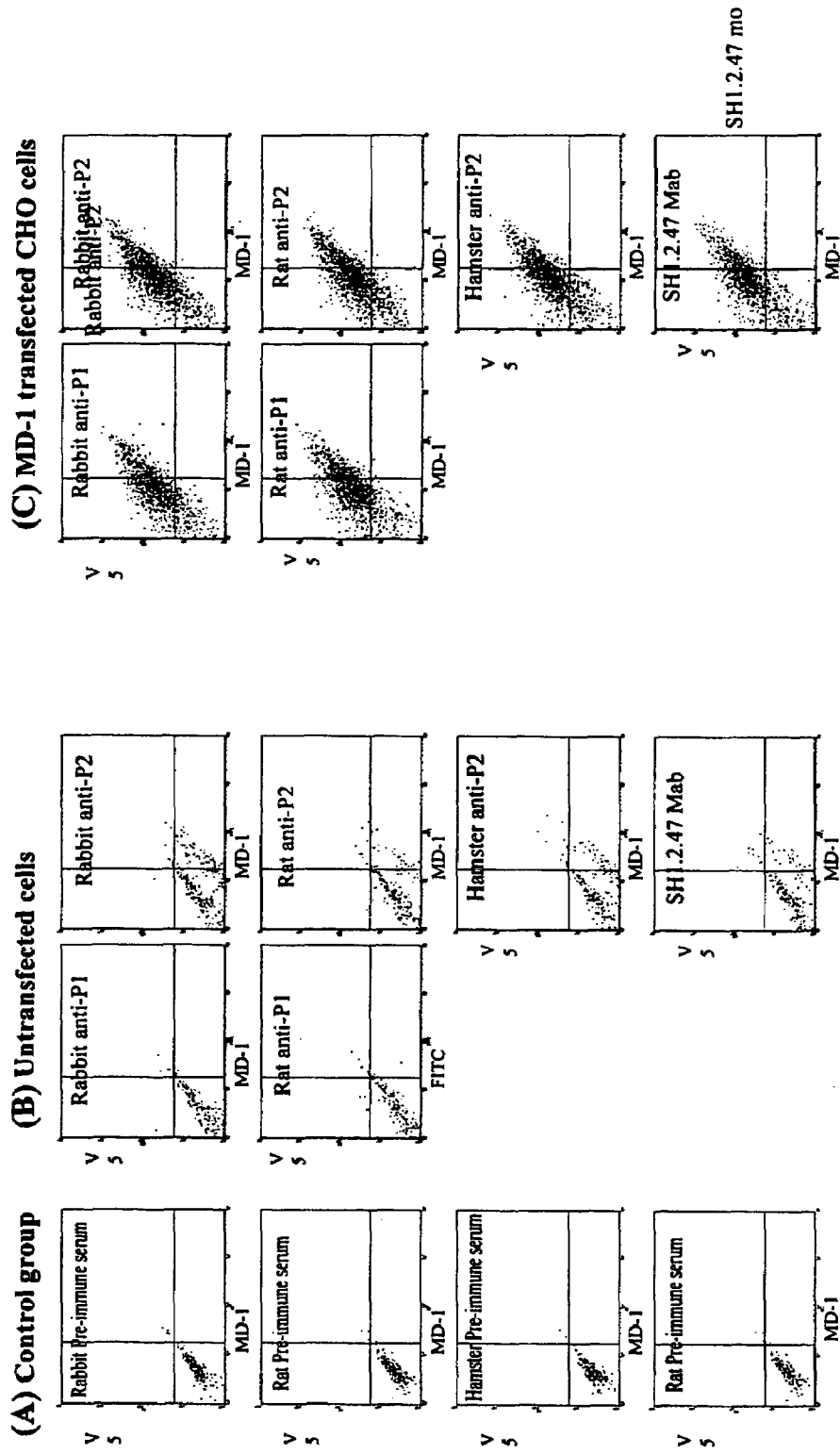
FIG. 6 is a FACS staining of MD-1 transfected CHO cells by anti-MD-1 antibodies. Panel B shows staining of control CHO cells incubated with rabbit or rat α-P1 or -P2 serum in the first and second rows respectively, with hamster α-P2 serum (third row), or with rat SH1.2.47 monoclonal α-P2 (fourth row). After incubation with first antibody, cells were stained with an appropriate FITC conjugated second Ig. Panel C represents equivalent data using MD-1 transfected CHO cells. Cells were also stained with an anti-flag/Tag Ig (α-V5 epitope) and a secondary PE conjugated Ab, shown as FL2 on the ordinate of each panel. Staining with pre-immune sera is shown only for MD-1 transfected CHO cells in panel A; similar control data (not shown) were obtained with untransfected CHO cells.

To define further the specificity of the sera above, the inventors performed FACS analysis, using untransfected CHO cells, and CHO cells transfected with a cDNA construct encoding murine MD-1, along with the various antibodies shown in FIG. 5. ~90% of the transfected CHO cells were positively stained with an anti-V5 (tag epitope) antibody (data not shown). All of the putative α-MD-1 sera bound specifically the transfected but not the non-transfected CHO cells (FIG. 6—typical data from one of 4 studies).

Figure 7:
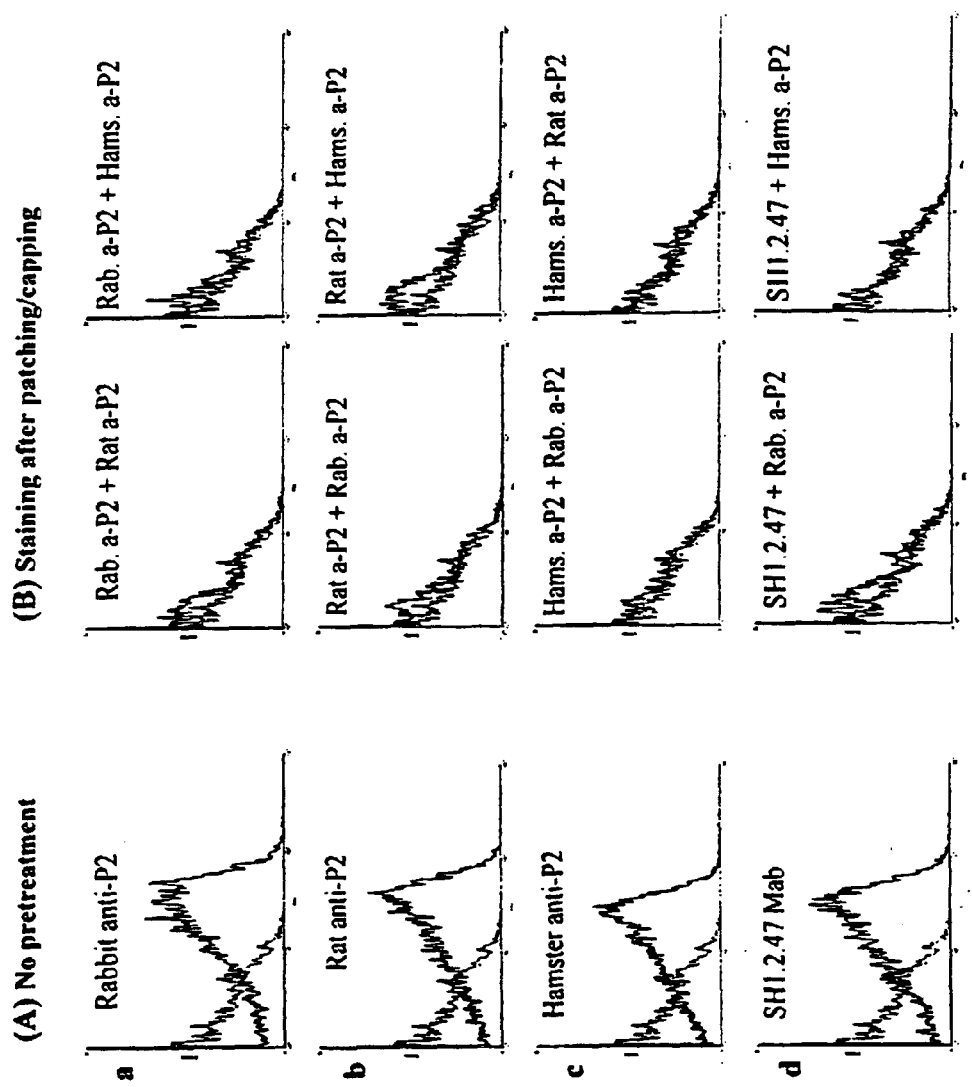
FIG. 7 is a FACS analysis showing patching/capping with any given α-MD-1 Ab, followed by α-rabbit, -rat or -hamster Abs, inhibits binding of all heterologus α-MD-1 Abs. In rows a-d, LPS-stimulated spleen cells were stained with rabbit (a), rat (b), hamster (c) or S H1.2.47 monoclonal (d) Abs and an appropriate FITC conjugated secondary Ab. Cells in column A did not receive any other treatment before staining. Cells in column B were pre-incubated with the α-MD-1 shown in column A, followed by incubation at 37° C./1 hr with α-rabbit, -rat or -hamster (H&L) Ig. Subsequently washed cells were re-stained with the two different test α-MD-1 Abs indicated in the 2 columns shown in B.

Crosslinking of LPS-stimulated T-Depleted Spleen Cells with α-MD-1 Abs Abolishes Subsequent Staining of Cells with all Putative α-MD-1 Abs Tested As confirmation that all of the heteroantisera, and the monoclonal SH1.2.47 antibody, detected the same (MD-1) molecule, we assessed the effect of "patching and capping" the serologically recognized epitope(s) on LPS stimulated cells on subsequent FACS staining using a different anti-MD-1 antibody. Target cells were T-depleted LPS stimulated mouse spleen cells. After initial incubation for 1 hr at 4° C. with one of the anti-MD-1 antibodies described, a cross-linking antibody was added (e.g. anti-hamster Ig following use of hamster anti-MD-1), and cells were incubated at 37° C. for 90 minutes to patch, cap and internalize the antigen(s) detected. Cells were washed thoroughly, returned to 4° C., and stained as in FIG. 6 for FACS analysis with a different anti-MD-1 Ig, and the appropriate FITC-anti-Ig. As shown in FIG. 7 (data from one of 2 experiments), pretreatment with any of the antibodies shown in FIG. 6 abolished the FACS staining with all antibodies (see control cells shown in first column of FIG. 7), further confirming their cross-reactivity.

Modulating Effects of the α-MD-1 Abs on In-Vitro Cytokine Production in MLR

In a final experiment the inventors asked whether the Abs described could modify cytokine production in allo-stimulated cells in MLR in vitro. Data in FIG. 8 (one of 3 studies) confirm results reported in Example 1, and show that responder spleen cells stimulated in the presence of either of rat, rabbit or hamster α-MD-1 polyclonal Abs, or the SH1.2.47 monoclonal α-MD-1, produce decreased levels of IL-2 and IFNγ in comparison with control cultures, but markedly increased IL4 and IL-10 levels. This inhibition was dose-dependent, and was lost at dilutions of ~1:5000 for polyclonal Abs and ~1:10 for SH1.2.47 mAb.

Discussion

Figure 8:
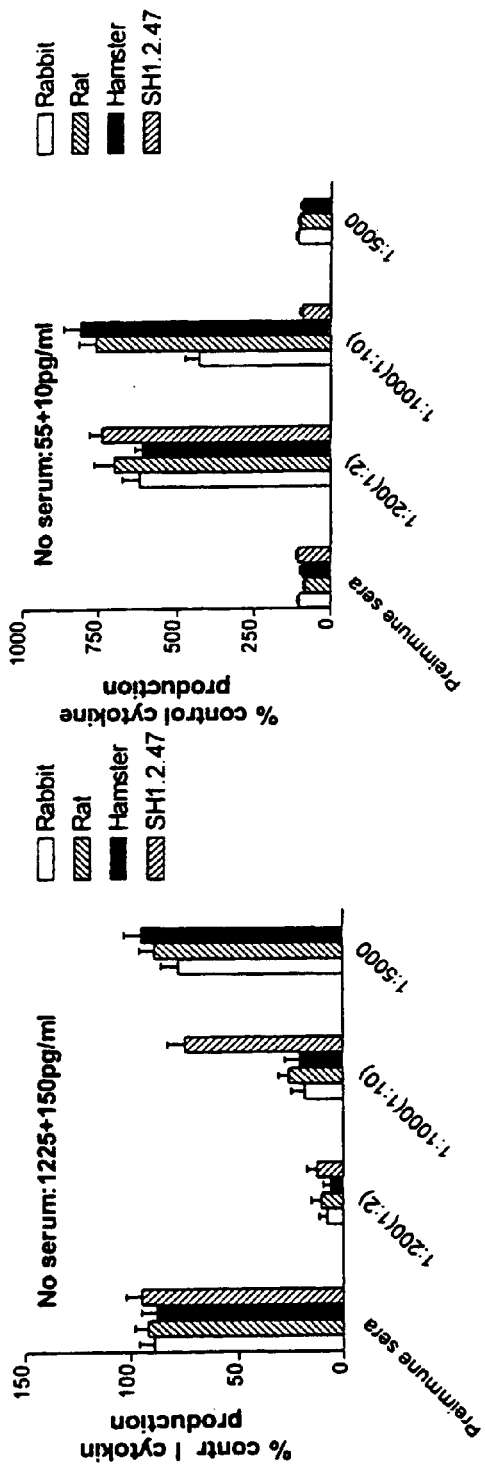
FIG. 8 are graphs showing α-MD-1 Ab included in MLR cultures inhibits IL-2 and IFN-γ production but enhances IL-4 and IL-10 production. Either heterologous α-MD-1 serum, or monoclonal SH1.2.47 Ab, was added at the dilutions shown in triplicate to C3H anti-C57BU6 MLR cultures. Data show cytokines (pg/ml or ng/ml) detected in culture supernatants at 40 hrs (mean±SD of 3 determinations). The detection limit for each cytokine in ELISA was ~30 pg/ml (10ng/ml for IL-10). For mAb SH.1.2.47 in ELISA assays, the two treatment groups received either a 1:2 or a 1:10 dilution of Ab (see axis of Figure).

The inventors have prepared antibodies to murine MD-1, in order to characterize the immunoregulation by MD-1 further. The data in this paper confirm that despite the sequence conservation of MD-1 across species (26,30) a number of different animal species can be used to produce antisera to murin MD-1. Thes sera detect a molecule expressed on dendritic cells, macrophages and B cells (data not shown). As shown in FIG. 8, in MLR cultures, functional blockade of MD-1 expression results in inhibition of IL-2 and IFNγ production (both type-1 cytokines) and marked stimulation of expression of IL-4 and IL-10 (type-2 cytokines). These results were not simply related to a slowed kinetics of production of IL-2/IFNγ (unpublished data-see Materials and Methods). The inventors have observed a similar effect of infusion of anti-MD-1 Abs in vivo as described in Example 3. This finding has implications for manipulation of a number of clinically relevant situations in vivo where cytokine changes are believed to contribute to immunopathology, including transplantation, allergy and autoimmune disorders.

Taken together, our data support the general concept that MD-1 is implicated in the delivery of costimulatory signals for T cell activation, a function which is in opposition to that suggested for the regulatory molecule OX-2.

Example 3

In Vivo Data Showing Anti-MDI Increases Allograft Survival Example 3

The inventors undertook experiments to determine whether there is a synergistic effect between portal vein immunization with allogeneic dendritic cells and blockage of MD-1 surface expression using an antibody to MD-1 in a mouse renal allotransplant model. For these experiments, groups of mice (n=6) were utilized and survival rates and cytokine production were monitored daily.

Figure 9:
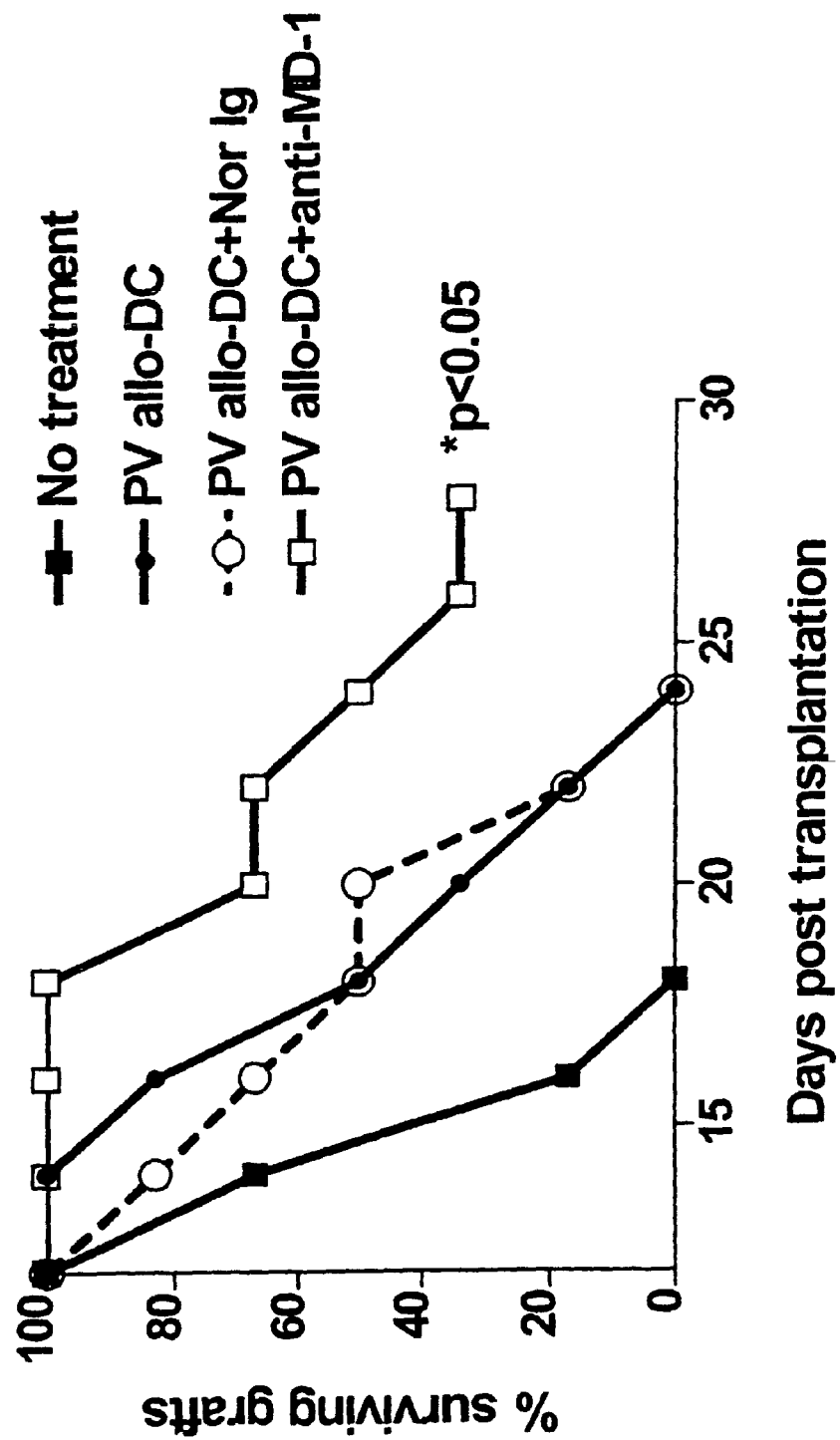
FIG. 9 is a graph showing synergy between pV immunization and anti-MD-1 antibody in increasing allograft survival.

As shown in FIG. 9, mice treated with dendritic cell infusion through the portal vein and subsequently treated systemically (intravenously) with an antibody to MD-1 had enhanced survival compared to mice which were also infused with allodendritic cells and an irrelevant isotype antibody, or infused with allodendritic cells through the portal vein, or not treated at all. The conclusion from these experiments is that the infusion of allodendritic cells and inhibition of MD-1 leads to enhanced survival compared to portal vein infusion of allodendritic cells without inhibition of MD-1. These data are consistent with a role for MD-1 as a molecule that can increase immune response, and further confirms utility of the use of an antibody to MD-1 to inhibit this effect.

Figure 10:
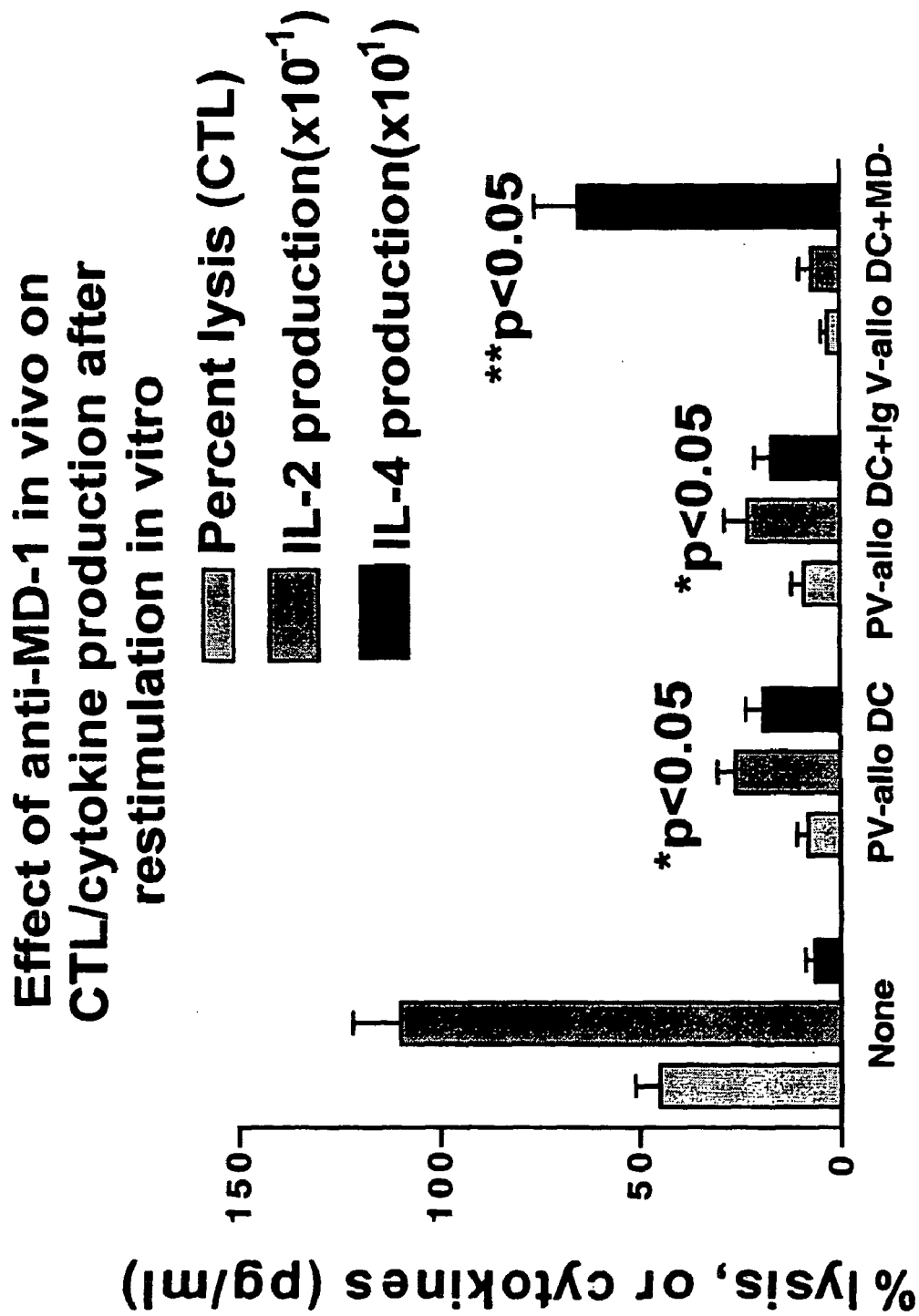
FIG. 10 is a graph showing the effect of anti-MD-1 in vivo on CTL-cytokine production after restimulation in vitro.

FIG. 10 provides in vitro data to support the in vivo result shown in FIG. 9. The ability of antibody to MD-1 to inhibit Th-1 cytokine production (IL-2), cytotoxic T-cell lysis (% lysis) and enhance Th-2 cytokine production (IL-4) is shown utilizing the same four groups studied in FIG. 9. In these experiments the combination of portal vein dendritic cell infusion and anti-MD-1 had a marked positive effect compared to either treatment alone.

Figure 11:
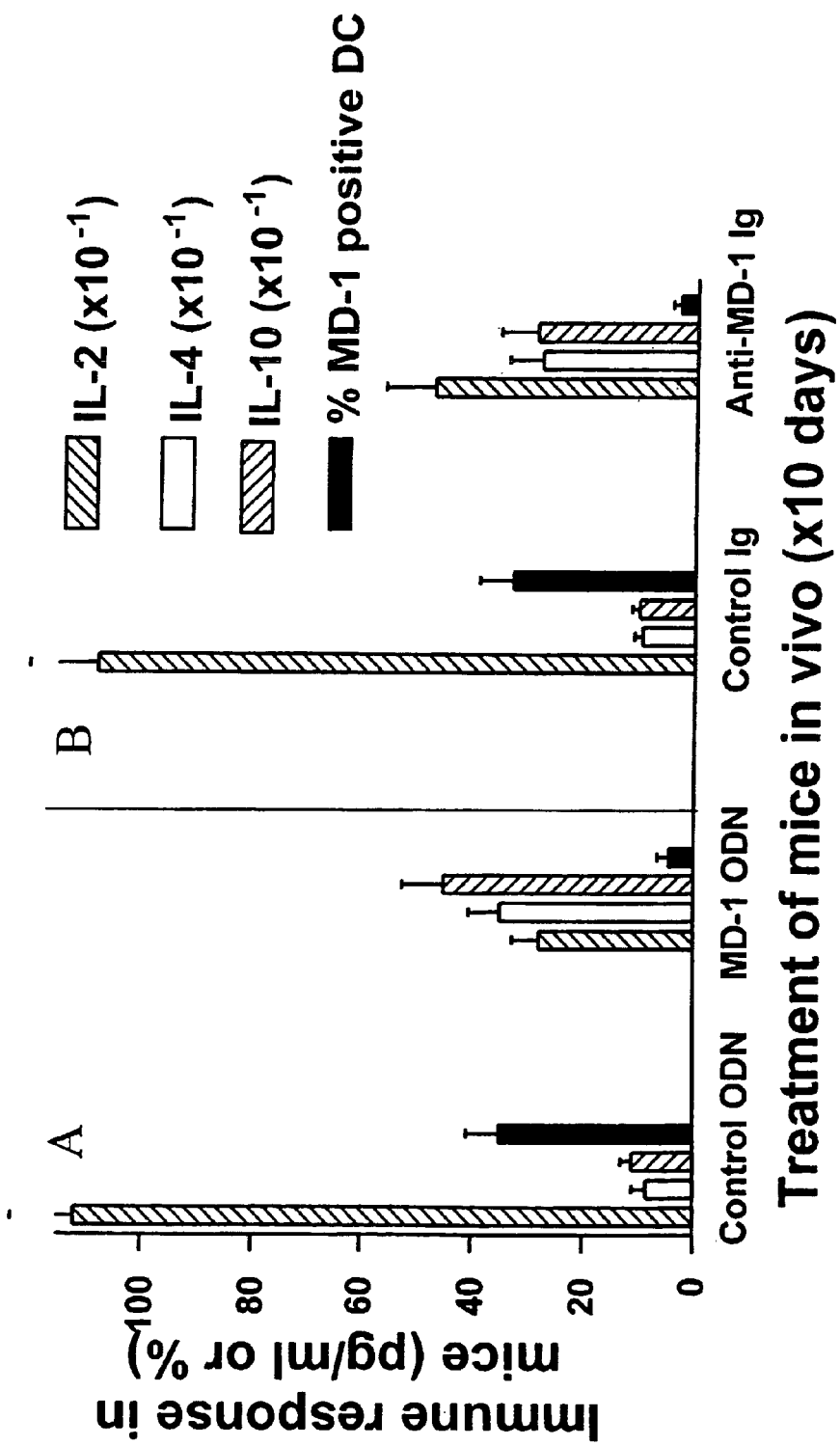
FIG. 11 is a graph showing the effect of in vivo treatment of transplanted mice with anti-MD reagents on cytokine and MD expression.

FIG. 11 demonstrates the effect of inhibition of MD-1 by the use of either an antisense oligonucleotide (OD-1) or antibody to MD-1. In this series of experiments, the use of the oligonucleotide (FIG. 11A) demonstrates that the antisense oligonucleotide resulted in a decrease in MD-1 expression in splenic mononuclear cells, enhanced production of IL-10 and IL-4 cytokines, and inhibition of IL-2. The use of an antibody to MD-1 (FIG. 11B) had a similar beneficial effect, with a decrease of MD-1 positive cells, a decrease in IL-2, and an enhanced expression of IL-4 and IL-10. These data again support the use of a blockage of MD-1 to improve allograft survival.

Example 4

Role of MD-1 in Fertility

Mammalian viviparous reproduction in an outbred population involves prolonged contact between antigenically foreign fetal cells and the immune system of an immunologically competent mother. Understanding the cellular and molecular basis for success or failure of the feto-maternal relationship in pregnancy may be pertinent to similar processes, such as survival or failure of allografts, parasitism, the success of neoplasms, and evolutionary selective mechanisms that have at their core the successful propagation of genes. Th1-type cytokines can play an important role in rejection in these situations, and especially in pregnancy. The inventors have determined that it is that the degree of exposure to bacterial lipopolysaccharide (LPS) provided by bacterial flora normally present in the intestine that is the key factor determining the risk of pregnancy failure, and that LPS acts via MD-1.

The variation in spontaneous abortion rates in the CBA×DBA/2 matings had remained unexplained for many years. CBA/J female mice which achieved 40% abortion rates in an INSERM colony in Paris, France, gave only 10-20% abortion rates when stock was flown to my McMaster colony, bred, and tested. The inventors suspected differences in bacterial flora might be responsible. A study of spontaneous abortions C.B-17 mice (in a SCID mouse barrier colony), where fibrin deposition and vascular occlusion signified the importance of clotting in pregnancy loss, showed a 15-20% abortion rate on a bacterially-defined Schaedler flora (32); high rates of abortion (≅40%) correlated with appearance of an unexpected bacterium in the flora, indicative of a break in the barrier (32). Bacterial endotoxin (LPS) is known to be a powerful abortogen in mice, and stimulates production of Th1 cytokines such as TNF-α, IL-1, IFN-γ (33). The drug indomethacin increases intestinal permeability, and abortion rates in CBA/J×DBA/2 mated mice, while treatment with the antibiotic, tetracycline, abrogated abortions (34). NK cell activity in mice has also been reported to depend on stimulation by bacterial flora (35); NK cells are, of course, an important source of certain Th1 cytokines. Recent data provide further evidence that LPS derived from bacterial flora plays a key role in the CBA×DBA/2 model beyond simply increasing Th1/Th2,3 ratios, or NK cell/macrophage activity, and MD-1 is involved in the response to the bacterial flora.

Figure 12:
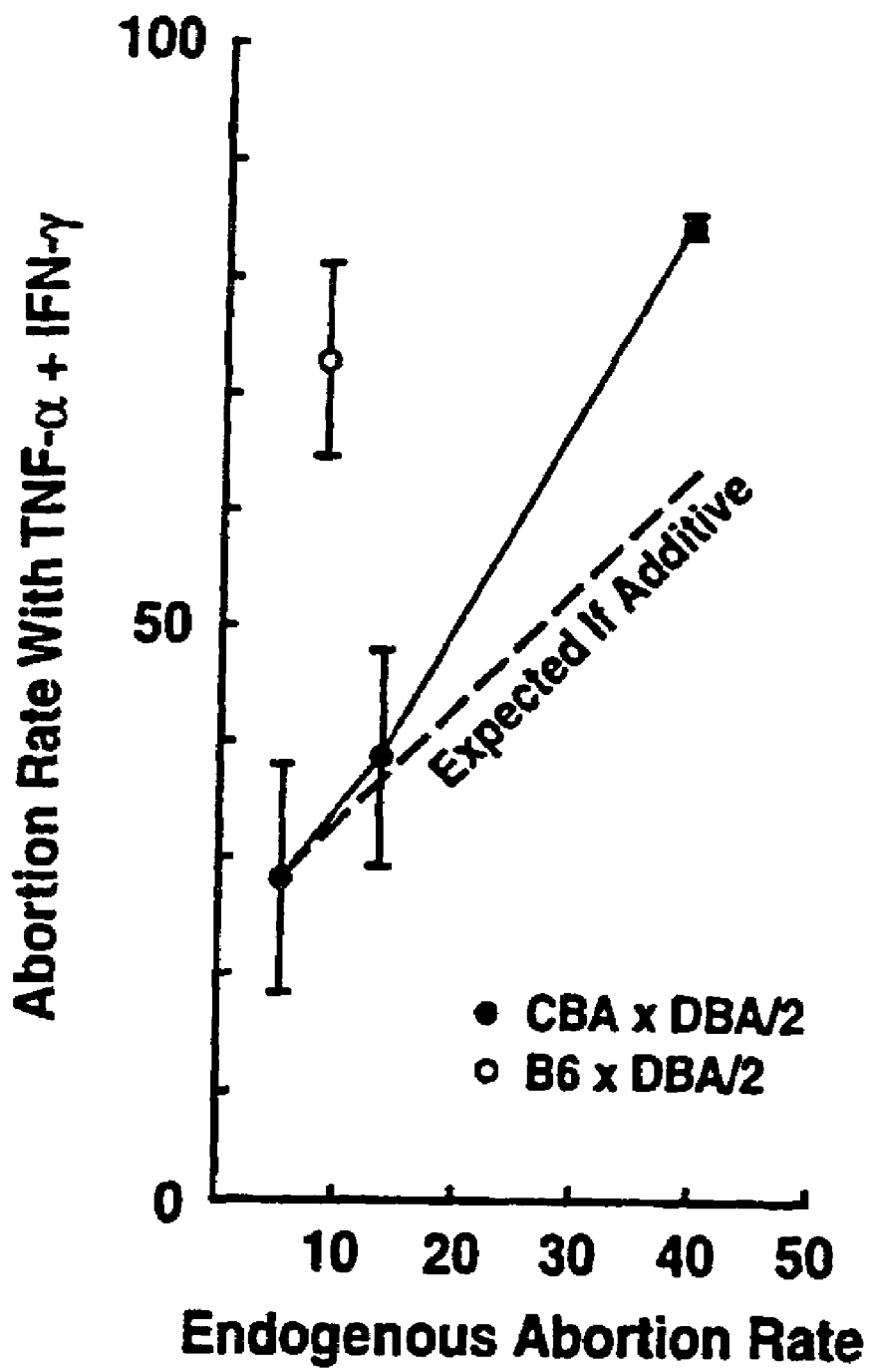
FIG. 12 is a graph showing a comparison of abortion rate following a gestation day injection of 1000 u rmIFN-γ+2000 u rhTNF-α to endogenous spontaneous abortion rate.
Figure 13:
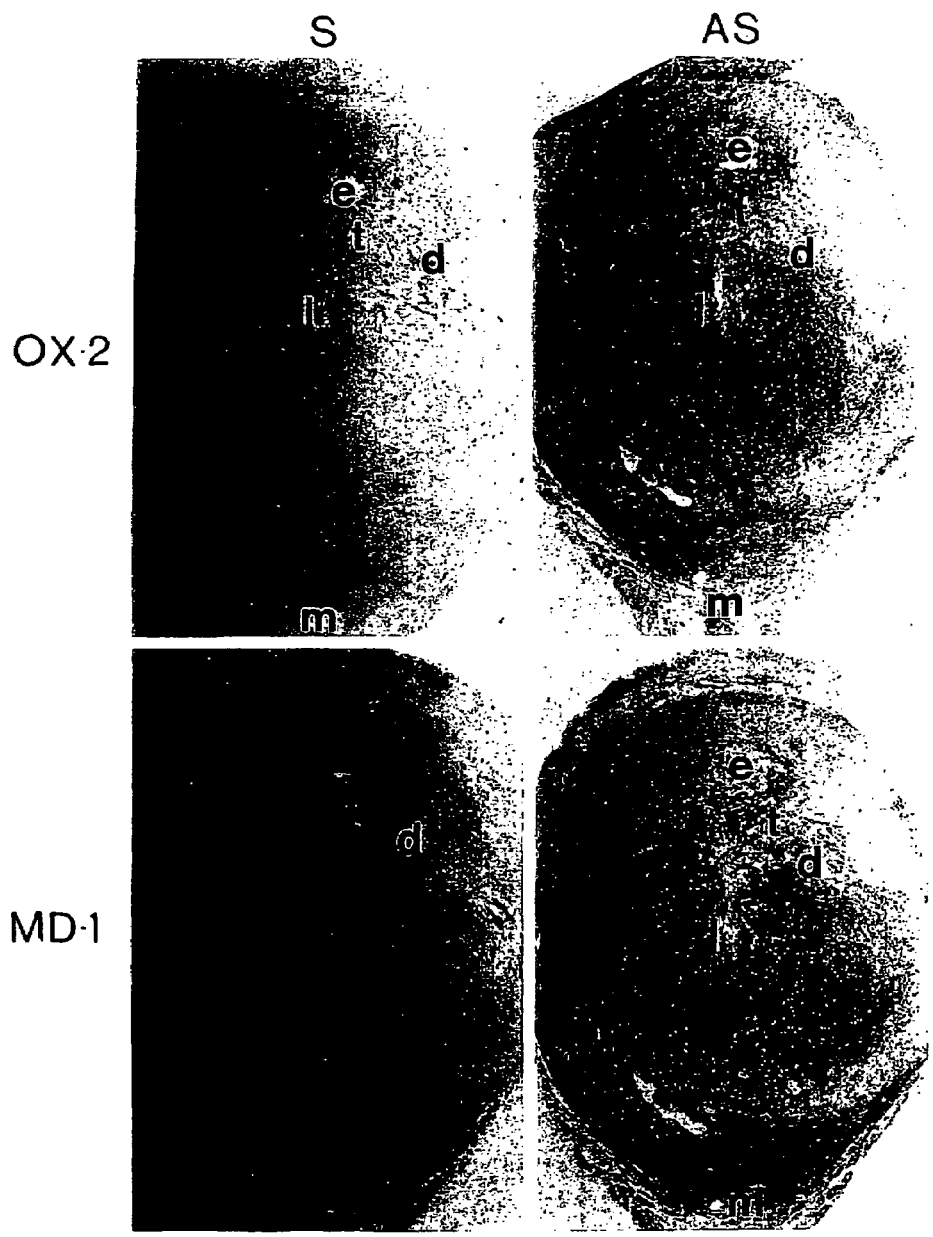
FIG. 13 are graphs showing the effect on abortion rates in CBAxDBA/2 matings of increasing dose of cytokines injected on gestation day (gd) 7.5.

The first clue that Th1 cytokines, and Th1/Th2,3 balance was not sufficient to understand pregnancy came from lack of close correlation of TNF-α/TGF-β2 ratios with abortion rates; an experimental perturbation in the ratio predicted the effect on abortion rates, but not the basal rate (23). Second, as illustrated in FIG. 12, abortion rates after an injection of TNF-α+IFN-γ on gd 7.5 could vary from 28% to >85%, depending on the basal rate of loss. One could suggest this might be due to the fact that with a higher basal loss rate, endogenous levels of TNF-α+IFN-γ should be higher, so injecting these cytokines would have an additive effect. The observed increase was, however, less than expected. Pharamacological dose-response curves tend to have even steeper slopes. When the inventors directly tested the dose-response curve in their mice, as shown in FIG. 13, the effect of higher cytokine doses seemed to plateau. Thus, an additional factor was needed for high abortion rates, such as noted in FIG. 12 for the mice studied in Paris (abortions >85%).

As mentioned previously, the inventors determined that MD-1 is an immune regulatory molecule involved in graft rejection. MD1 is a membrane-associated molecule which binds to and stabilizes pattern recognition receptors (PRR) for pathogen-related 'danger' signals such as LPS (Example 1). LPS is a potent mitogen for B lymphocytes, and MD-1 associated with the RP105 pattern recognition receptor (PRR) which reacts with LPS (26). CD14 is a PRR on macrophages, and blocking synthesis of MD-1 with specific oligodeoxynucleotide (ODN) down-regulated expression of CD14 (Example 1). It has not been possible to show that MD-1 and CD14 physically associate by capping, perhaps because the association is a weak one. LPS binding to CD14 is facilitated by a serum LPS binding protein, and soluble CD14 (sCD14) may facilitate as well (37,38); binding CD14 does not signal the cell, for CD14 lacks an ITAM (41). Rather CD14+LPS causes an association with CD11c/CD18 and ultimately the toll-like receptor, Tlr4, which does possess the ITAM signaling motif. LPS-associated protein can bind to Tlr2, and certain bacteria such as *Salmonella* may signal via Tlr5 (33,39). MD-2 is another membrane stabilizer associated with tlr2 and tlr4 (Example 2). Tlr4 is particularly relevant to the triggering of abortions in the CBA×DBA/2 model, because Tl4-deficient C3H/HeJ mice do not abort in response to LPS.

The inventors studied expression of mRNA for fgl2 and CD200 (OX-2) in the uterus of CBA×DBA/2 matings, and found CD200 mRNA in the same areas as fgl2 on gd 8.5 (40). Parallel experiments analyzing in situ staining for MD-1 mRNA, shown in FIG. 5, demonstrated MD-1 mRNA in the same areas as CD200 (and fgl2, see FIG. 14). Further, an injection of TNF-α+IFN-γ on gd 7.5 reduced CD200 mRNA detection, but increased detection of fgl2 and MD-1 staining (40 and unpublished data). When rabbit anti-MD-1 antibody was also injected on gd 7.5, the ability of cytokines to abort the mice was abolished (FIG. 15). The original studies which led to the discovery that TNF-α+IFN-γ had to abort by up-regulating procoagulant in maternal decidua had included studies with IRF1$^{-/-}$ mice (B6.129-Irf1$^{tm1Mak}$) (20); IRF1$^{-/-}$ females bearing IRF1$^{+/-}$ embryos could not be aborted by injecting TNF-α+IFN-γ on gd 7.5. These knockout mice are susceptible to toxic death if TNF-α+IFN-γ are injected at a sufficient dose, but are resistant both to LPS stimulation of TNF-α/IFN-γ production and to LPS-induced death (45). Taken together, the data suggest that TNF-α+IFN-γ cause abortions by increasing LPS levels, by rendering the intestine more permeable, and abortions are produced by LPS acting in the uterus rather than by an effect at the maternal-fetoplacental interface of the injected cytokines.

Figure 14:
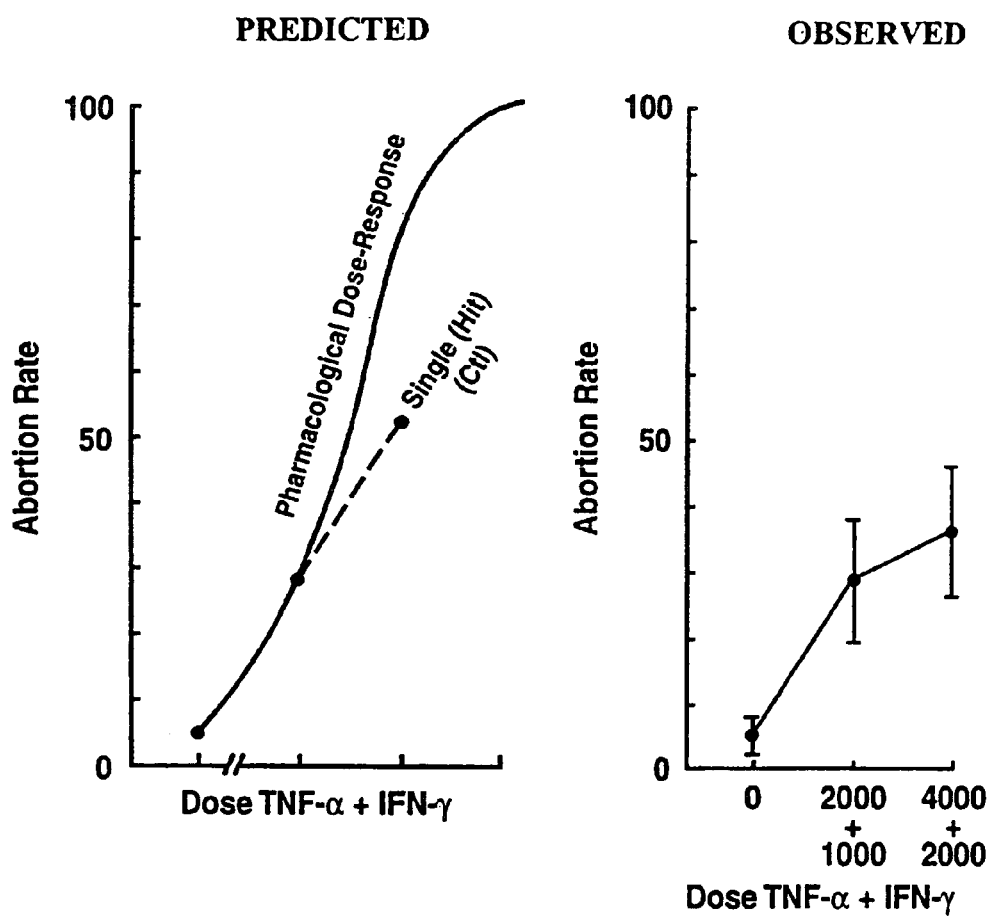
FIG. 14 shows in situ hybridization of gestation day (gd) 8.5 implanation site for CBAxDBA/2 mating.
Figure 15:
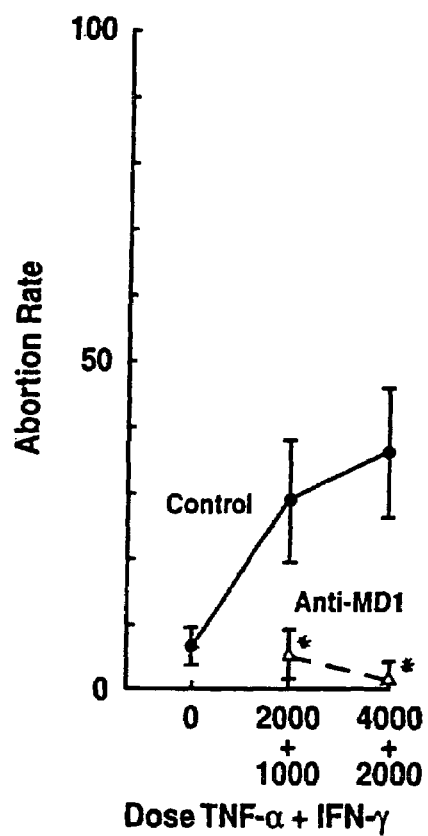
FIG. 15 is a graph showing the effect of 200 µl rabbit anti-MD-1 (P2 epitope) on cytokine-boosted abortion rate in CBAxDBA/2 mated mice. Interfering with an MD-1-dependent signal prevented cytokine-dependent loss; abortions are known to depend on these cytokines even in animals which have not received an injection to boost loss rates.

FIG. 14 is an in situ hybridization compating OX-2 (CD200) to MD-1 hybridization pattern. Briefly, CBA/J female mice obtained from the Jackson Labs, Bar Harbor Me. were mated at age 8-10 weeks with DBA/2 males, in a barrier facility with 12 hr light/dark cycle+lab chow and water ad lib, and on day 8.5 of gestation, the mice were sacrificed and the uteri removed and fixed in 4% freshly prepared paraformaldehyde. After 18-24 hrs, the uteri were transferred to 70% ethanol, and then were pocessed from embedding in paraffin, using standard methods. Five micron sections were cut and fixed to Aptex-coated slides. In situ hybridization was carried out using digoxigenin-11-UTP-labeled cRNA probes (sense and anti-sense) synthesized after subcloning the relevant fragment of murine OX-2 (CD200) or murine MD-1. The OX-2 riboprobes were prepared using a 501 bp fragment subcloned into the PBK vector with T3 promotor (for sense) being 5'-CCGTCGAC-CAAGTGGAAGTG-3' (SEQ. ID. NO. 6), and T7 promotor (for antisense) being 5'-ACGGATCCTTGTCCAGACCT-GCTT-3' (SEQ. ID. NO. 7) (Chen Z, Zeng H, Gorczynski R M. Biochem Biophy Acta 1997; 1362:6-10). The MD-1 riboprobes were prepared using a 498 bp fragment subcloned into the PBK vector with the T3 promotor being 5'-ATACTCGACGCCGCCACCATGTGACCATGGCA-GCGAAAA-3' (SEQ. ID. NO. 8) and the T7 promotor being 5'-ATCGGATCCCTAGGTGAGTCCAGGGAC-3' (SEQ. ID. NO. 9).

The digoxigenin-UTP-labelled probe concentration was determined by immunoenzymatic reaction with chemiluminescent detection, and the probes were stored at −80 C. For in situ hybridization, the standard method was as follows (Clark D A, Ding J-W, Yu G, Levy G A, Gorczynski R M. Molecular Human Reproduction 2001; 7:185-194): Tissue sections were deparaffinized in 100% xylene, 100% alcohol, followed by prehydration in 50% formamide in 2×SCC at 22 C for 1 h. Hybridization mixture was 50% deionized formamide, 5% dextran sulfate, 250 ug/ml salmon sperm DNA, and 2 ug digoxigenin-labeled cRNA probe in 2×SCC (17.53 g NaCl+8.82 g Na citrate in 1 l DH20 pH 7.0). This mixture was denatured by heating in an 85° C. water bath for 5 minutes followed by chilling on ice for for 1 minute, and was then placed on the tissue sections and incubated at 42° C. overnight. Post-hybridization washing in 2×SCC, followed by incubation in 3% blocking reagent (normal goat serum) followed after a brief wash by alkaline phosphatase-conjugated polyclonal goat anti-digoxigenin IgG Fab'2 fragment at a 1/500 dilution in Tris-HCI buffer (pH 7.5). After 2 washes of 5 minutes in fresh buffer, 5-bromo-4-chloro-3-indoxyl-phosphate (BCIP) and nitroblue tetrazolium (NBT) were added ind incubated for approximately 2 h. The sections were washed and counterstained 5 min with Methyl Green, dehydrated, and mounted in Permount for viewing. Photographs were taken at ×25, ×100, ×250 and ×400 magnification using Kodak 100 ASA colour print film and an automatic exposure metered system (WILD Photoautomat MPS45).

For FIG. 15, CBA/J female mice mated to DBA/2 males, as described above, were sacrificed on day 13.5 of gestation, and the number of normal and resobing embryos was recorded. Groups of 3-10 mice were used, depending on availability and success of the mating procedure. In some experiments, on day 7.5 of getstation, the mice were injected intrap ritoneally with 0.2 ml phosphate buffered saline (PBS) containing 2000 iu rhTNF-alpha+1000 IU rminterferon-gamma (Gibco BRL), or 0.4 ml 4000 iu TNF-α+2000 iu IFN-γ. The control group was untreated as previous data have shown that sham injection in the range of 0.1-0.3 ml PBS or normal rabbit serum or control mAbs has no significant effect on endogenous or cytokine-boosted abortion rates (Clark D A, Crit. Rev. Immunol. 1991; 11:215-247; Clark D A, Chaouat G, Arck P C, Mittruecker H W, Levy G A. J. Immunol. 1998; 160:545-549; Arck P C, Ferrick D A, Steele-Norwood D, Egan P J, Croitoru K, Carding S, Dietl J, Clark D A. Cellular Immunology 1999; 196:71-79). Rabbit polyclonal antibody to the P2 epitope of MD-1 able to abrogate production of IL-2 and interferon-gamma from a C3H mouse spleen cell anti-C57BI/6 mixed leukocyte reaction at a dilution (titre) of 1/1000 (see Example 2), was injected into the mice at the same time as the TNF-alpha+ IFN-gamma. The group mean +/−1 sem is shown. Statistical significance (P<0.05 denoted by *) was determined using Chi-square or Fisher's Exact test, where appropriate.

The above results demonstrate that MD-1 is an important immune modulator that plays a significant role in fertility. Effectively modulating MD-1 can lead to novel therapies to treat or prevent recurrent miscarriages.

Further the results show that inhibiting MD-1 can inhibit the effects of LPS. As a result, modulating MD-1 may also be useful in: inhibiting production of antibodies by B lymphocytes (e.g. inhibiting antibody-mediated autoimmunity); inhibiting activation of dendritic cells (DC) that promote pro-inflammatory graft rejection (and cell-mediated autoimmunity e.g. rheumatoid arthritis); and in inhibiting processes that lead to septic shock and organ dysfunction in critically ill patients.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

DC incubated with anti-sense ODNs to MD-1 fail to stimulate proliferation or induction of CTL/type-1 cytokines in allogeneic responder cells

| Added[a] | $^3$HTdR (cpm)[b] | Percent lysis $^{51}$Cr targets[c] | | Cytokines in culture (pg/ml)[d] | | |
|---|---|---|---|---|---|---|
| ODNs | | (50:1, effector:target) | IL-2 | IL-4 | IFNγ | IL-10 |
| NONE | 9920 ± 1400 | 44 ± 5.7 | 1080 ± 190 | 60 ± 20 | 890 ± 140 | 45 ± 15 |
| ODN-1 | 1220 ± 190* | 6.4 ± 2.2* | 180 ± 60* | 105 ± 20* | 125 ± 45* | 120 ± 30* |
| ODN-3 | 8550 ± 1350 | 38 ± 6.1 | 1135 ± 175 | 55 ± 20 | 770 ± 130 | 40 ± 20 |

Footnotes:

[a]C57Bl/6 bone marrow derived DCs were incubated with medium alone (control-first row) or with one of 2 different anti-sense ODNs to MD-1 (see Materials and Methods, and Legends to FIGS. 1-3). After further overnight stimulation with LPS, cells were washed thoroughly, treated with mitomycin C, and used as stimulators in triplicate cultures (3:1 responder stimulator ratio) for C3H spleen cells (pooled from 4 stock mice). Cultures were harvested and tested as described earlier for proliferation, CTL production or cytokine production.

[b]$^3$HTdR incorporation (mean ± SD) for cultures assayed in triplicate at 72 hrs. $^3$HTdR incorporation in control cultures with no DC stimulator cells was 980 ± 230.

[c]Percent lysis (50:1, effector:target) using cells from 5 day cultures with 1 × 10$^4$ $^{51}$Cr C57BL/6 spleen ConA blast targets.

[d]Cytokines (pg ml−1) in culture supernatants harvested at 60 hrs.

*p < 0.05 compared with control in first row

TABLE 2

DC incubated with anti-sense ODNs to MD-1 induce cells able to suppress antigen-specific proliferation or induction of CTL/type-1 cytokines in allogeneic responder cells

| Added[a] | ³HTdR (cpm)[b] | Percent lysis ⁵¹Cr targets[c] | | Cytokines in culture (pg/ml)[d] | | |
|---|---|---|---|---|---|---|
| ODNs | | (50:1, effector:target) | IL-2 | IL-4 | IFNγ | IL-10 |
| Secondary cultures stimulated with C57Bl/6 DC | | | | | | |
| Control | 8220 ± 1150 | 38 ± 4.8 | 1120 ± 210 | 50 ± 15 | 920 ± 120 | 40 ± 15 |
| NONE | 9200 ± 1250 | 35 ± 5.2 | 1010 ± 165 | 70 ± 20 | 990 ± 145 | 55 ± 20 |
| ODN-1 | 2820 ± 550* | 12 ± 4.2* | 290 ± 90* | 245 ± 60* | 305 ± 85* | 170 ± 45* |
| ODN-3 | 8900 ± 1405 | 35 ± 6.0 | 1065 ± 225 | 75 ± 20 | 855 ± 150 | 60 ± 25 |
| Secondary cultures stimulated with BALB/c DC | | | | | | |
| Control | 9100 ± 1210 | 40 ± 5.1 | 1010 ± 230 | 50 ± 20 | 810 ± 130 | 55 ± 20 |
| NONE | 9720 ± 1550 | 42 ± 6.0 | 1230 ± 210 | 65 ± 15 | 920 ± 160 | 45 ± 15 |
| ODN-1 | 8200 ± 1190 | 44 ± 5.9 | 980 ± 160 | 55 ± 20 | 845 ± 155 | 60 ± 20 |
| ODN-3 | 8990 ± 1050 | 39 ± 5.7 | 1035 ± 195 | 60 ± 20 | 870 ± 190 | 55 ± 25 |

Footnotes:
[a]C57Bl/6 bone marrow derived DCs were incubated with medium alone (NONE) or with one of 2 different anti-sense ODNs to MD-1 (see Materials and Methods, and footnotes to Table 1). After further overnight stimulation with LPS cells were washed thoroughly, treated with mitomycin C, and used as stimulators in triplicate cultures (3:1 responder stimulator ratio) for C3H spleen cells (pooled from 4 stock mice). Cells were harvested at 5 days, washed and counted. $2 \times 10^6$ cells were added in triplicate to secondary cultures containing $5 \times 10^6$ C3H responder cells and $2 \times 10^6$ fresh C57Bl/6 or BALB/c DC. Control cultures received no added cells from the first culture.
[b-d]As for Table 1;
*p < 0.05 compared with control in first row

TABLE 3

Anti-OX-2 mAb inhibits suppression mediated by DC incubated with anti-sense ODNs to MD-1

| Added[a] | ³HTdR (cpm)[b] | Percent lysis ⁵¹Cr targets[c] | | Cytokines in culture (pg/ml)[d] | | |
|---|---|---|---|---|---|---|
| ODNs | | (50:1, effector:target) | IL-2 | Il-4 | IFNγ | IL-10 |
| Control rat antibody added to cultures receiving ODN-treated DC: | | | | | | |
| Control | 9520 ± 950 | 31 ± 3.9 | 1210 ± 190 | 65 ± 20 | 890 ± 160 | 45 ± 10 |
| NONE | 8650 ± 1050 | 32 ± 4.6 | 1150 ± 190 | 50 ± 15 | 960 ± 190 | 60 ± 20 |
| ODN-1 | 2350 ± 690* | 9.2 ± 3.6* | 330 ± 80* | 205 ± 45* | 220 ± 100* | 145 ± 55* |
| ODN-3 | 9490 ± 1285 | 30 ± 5.6 | 1220 ± 230 | 60 ± 20 | 935 ± 175 | 55 ± 20 |
| Anti-OX-2 mAb added to cultures receiving ODN-treated DC: | | | | | | |
| Control | 8970 ± 1340 | 33 ± 5.3 | 1320 ± 210 | 55 ± 15 | 950 ± 140 | 50 ± 15 |
| NONE | 9155 ± 1350 | 31 ± 4.6 | 1195 ± 160 | 50 ± 15 | 990 ± 175 | 55 ± 10 |
| ODN-1 | 7530 ± 1560 | 25 ± 4.8 | 885 ± 230 | 85 ± 25 | 690 ± 185 | 75 ± 25 |
| ODN-3 | 8360 ± 1285 | 31 ± 5.2 | 1100 ± 160 | 65 ± 20 | 825 ± 175 | 50 ± 15 |

Footnotes:
[b]C57Bl/6 bone marrow derived DCs were incubated with medium alone (NONE) or with one of 2 different anti-sense ODNs to MD-1 (see Materials and Methods, and footnotes to Tables 1 and 2). After overnight stimulation with LPS, the cells were washed thoroughly, treated with mitomycin C, and used as stimulators in triplicate cultures (3:1 responder stimulator ratio) for C3H spleen cells (pooled from 4 stock mice). Cultures in the upper half of the table were incubated in the presence of pooled normal rat Ig (10 mg/ml), while cultures in the lower half of the Table were incubated in the presence of 10 mg/ml anti-OX-2 (3B6). Cells were harvested at 5 days and added to fresh cultures containing $5 \times 10^6$ C3H responder cells and $2 \times 10^6$ fresh C57Bl/6 as in Table 2.
[b-d]As for Tables 1 and 2;
*p < 0.05 compared with control in first row.

FULL CITATIONS FOR REFERENCES REFERRED TO IN THE SPECIFICATION

1. Hathcock, K. S., G. Laszlo, C. Pucillo, P. Linsley, and R. J. Hodes. 1994. Comparative analysis of B7-1 and B7-2 costimulatory ligands:expression and function. *J. Exp. Med*. 180:631.
2. Inaba, K., M. Witmer-Pack, M. Inaba, K. S. Hathcock, H. Sakuta, M. Azuma, H. Yagita, K. Okumura, P. S. Linsley, S. Ikehara, S. Muramatsu, R. J. Hodes, and R. M. Steinman. 1994. The tissue distribution of the B7-2 costimulator in mice:abundant expression on dendritic cells in situ and during maturation in vitro. *J. Exp. Med*. 180:1849.
3. Larsen, C. P., E. T. Elwood, D. Z. Alexander, S. C. Ritchie, R. Hendrix, C. TuckerBurden, H. R. Cho, A. Aruffo, D. Hollenbaugh, P. S. Linsley, K. J. Winn, and T. C. Pearson. 1996. Long-term acceptance of skin and cardiac allografts after blocking CD40 and CD28 pathways. *Nature* 381: 434.
4. Vidard, I., K. L. Rock, and B. Benacerraf. 1992. Heterogeneity in antigen processing by different types of antigen-presenting cells: effect of cell culture on antigen processing ability. *J. Immunol* 149:1905.
5. Krieger, N. R., D. Yuh, W. B. McIntyre, T. F. Flavin, D. P. Yin, R. Robbins, and C. G. Fathman. 1998. Prolongation of cardiac graft survival with anti-CD4lg plus hCTLA4lg in primates. *J. Surg. Res*. 76:174.
6. Lin, H., J. C. Rathmell, G. S. Gray, C. B. Thompson, J. M. Leiden, and M. L. Alegre. 1998. Cytotoxic Telymphocyte antigen 4 (CTLA4) blockade accelerates the acute rejection of cardiac allografts in CD28-deficient mice: CTLA4 can function independently of CD28. *J. Exp. Med*. 188:199.
7. Sayegh, M. H., and L. A. Turka. 1998. Mechanisms of disease: The role of T-cell costimulatory activation pathways in transplant rejection. *N. Engl. J. Med*. 338:1813.
8. Uchikoshi, F., Z. D. Yang, S. Rostami, Y. Yokoi, P. Capocci, C. F. Barker, and A. Naji. 1999. Prevention of autoimmune recurrence and rejection by adenovirus-mediated CTLA4Ig gene transfer to the pancreatic graft in BB rat. *Diabetes* 48:652.
9. Yang, Z. D., S. Rostami, B. Koeberlein, C. F. Barker, and A. Naji. 1999. Cardiac allograft tolerance induced by intra-arterial infusion of recombinant adenoviral CTLA4Ig. *Transplantation* 67:1517.
10. Gorczynski, R. M., and W. Holmes. 1991. Specific manipulation of immunity to skin grafts bearing multiple minor histocompatibility differences. *Immunol. Lett*. 27:163.
11. Gorczynski, R. M., Z. Chen, S. Chung, Z. Cohen, G. Levy, B. Sullivan, and X.-M. Fu. 1994. Prolongation of rat small bowel or renal allograft survival by pretransplant transfusion and/or by varying the route of allograft venous drainage. *Transplantation* 58:816.
12. Gorczynski, R. M., Z. Chen, X. M. Fu, and H. Zeng. 1998. Increased expression of the novel molecule Ox-2 is involved in prolongation of murine renal allograft survival. *Transplantation* 65:1106.
13. Barclay, A. N. 1981. Different reticular elements in rat lymphoid tissue identified by localization of la, Thy-1 and MRC OX-2 antigens. *Immunology* 44:727.
14. Gorczynski, R. M., Z. Cohen, X. M. Fu, and J. Lei. 1999. Anti-rat OX-2 blocks increased small intestinal transplant survival after portal vein immunization. *Transpl. Proc*. 31:577.
15. Gorczynski, R. M., M. S. Cattral, Z. G. Chen, J. A. Hu, J. Lei, W. P. Min, G. Yu, and J. Ni. 1999. An immunoadhesin incorporating the molecule OX-2 is a potent immunosuppressant that prolongs allo- and xenograft survival. *J. Immunol*. 163:1654.
16. Gorczynski, L., Z. Chen, J. Hu, G. Kai, V. Ramakrishna, and R. M. Gorczynski. 1999. Evidence that an OX-2 positive cell can inhibit the stimulation of type-1 cytokine production by bone-marrow-derived B7-1 (and B7-2) positive dendritic cells. *J. Immunol*. 162:774.
17. Chan, V. W. F., I. Mecklenbrauker, I. Su, G. Texido, M. Leitges, R. Carsetti, C. A. Lowell, K. Rajewsky, K. Miyake, and A. Tarakhovsky. 1998. The molecular mechanism of B cell activation by toll-like receptor protein RP-105. *J. Exp. Med*. 188:93.
18. Fugier-Vivier, I., O. de Bouteiller, C. Guret, F. Fossiez, J. Banchereau, M. G. Mattei, S. Ait-Yahia, E. Garcia, S. Lebecque, and Y. J. Liu. 1997. Molecular cloning of human RP105. *Eur. J. Immunol*. 27:1824.
19. Hoffmann, J. A., F. C. Kafatos, C. A. Janeway, and R. A. B. Ezekpowitz. 1999. Phylogenetic perspectives in innate immunity. Science 284:1313.
20. Adachi, Y., C. Satokawa, M. Saeki, N. Ohno, H. Tamura, S. Tanaka, and T. Yadomae. 1999. Inhibition by a CD14 monoclonal antibody of lipopolysaccharide binding to murine macrophages. *J. Endotoxin Res*. 5:139.
21. Medzhitov, R., P. Preston-Hurlburt, and C. A. Janeway. 1997. A human homologue of the Drosophila Toll protein signals activation of adaptiv immunity. *Nature* 388:394.
22. Ragheb, R., Abrahams, S., Beecroft, R., Hu, J., Ni, J., Ramakrishna, V., Yu, G. and Gorczynski, R.M. 1999. Preparation and functional properties of monoclonal antibodies to human, mouse and rat OX-2. *Immunol. Lett*. 68:311.
23. Fabrega, E., J. Crespo, F. Casafont, J. Delapena, G. Delasheras, J. A. Amado, and F. Ponsromero. 1995. Endothelin-1 and vascular complications in liver transplantation. *Transplantation* 59:1748.
24. Gilchrest, B. A., and V. A. Bohr. 1997. Aging processes, DNA damage, and repair. *FASEB J* 11:322.
25. Kohler, G., and C. Milstein. 1975. Preparation of monoclonal antibodies. *Nature* 25:256.
26. Miyake, K., R. Shimazu, J. Kondo, T. Niki, S. Akashi, H. Ogata, Y. Yamashita, Y. Miura, and M. Kimoto. 1998. Mouse MD-1, a molecule that is physically associated with RP105 and positively regulates its expression. *J. Immunol*. 161:1348.
27. Flanagan, W. M., and R. W. Wagner. 1997. Potent and selective gene inhibition using antisense oligodeoxynucleotides. *Mol. Cell. Biochem*. 172:213.
28. Lewis, J. G., K. Y. Lin, A. Kothavale, W. M. Flanagan, M. D. Matteucci, R. B. DePrinc, R. A. Mook, R. W. Hendren, and R. W. Wagner. 1996. A serum resistant cytofectin for cellular delivery of antisense oligodeoxynucleotides and plasmid DNA. *Proc. Natl. Acad. Sci. U.S.A*. 10000:00.
29. Akashi, S., H. Ogata, F. Kirikae, T. Kirikae, K. Kawasaki, M. Nishijima, R. Shimazu, Y. Nagai, K. Fukudome, M. Kimoto, and K. Miyake. 2000. Regulatory roles for CD14 and phosphatidylinositol in the signaling via toll-lik receptor 4-MD-2. *Biochem. Biophys. Res. Commun*. 268:172.
30. Miura Y, Shimazu R, Miyake K, Akashi S, Ogata H, Yamashita Y, Narisawa Y, Kimoto M. Blood. (1998) 92:2815.
31. Shimazu R, Akashi S, Ogata H, Nagai Y, Fukudome K, Miyake K, Kimoto M. J. Exp. Med. (1999) 189:1777.
32. Guha-Thakurta N, Majde J A. 1997. Early induction of proinflammatory cytokine and type I interferon mRNAs following Newcastle disease virus, poly [rI:rC], or low-dose LPS challenge of the mouse. J Interferon Cytokine Res 17:197-204.
33. Clark D A, Banwatt D, Chaouat G. 1993. Effect of prostaglandin synthesis inhibitors on spontaneous and endotoxin-induced abortion in mice. J Reprod Immunol 24:29-44.
34. Haller D, Blum S, Bode C, Hammes W P, Schiffrin E J. 2000. Activation of human peripheral blood mononuclear cells by nonpathogenic bacteria in vitro: evidence of N K cells as primary targets. Infect Immunity 68:752-759.
35. Gorczynski RM, Chen Z, Zeng H, Fu X M. 1997. Specificity for in vivo graft prolongation in γδ T cell receptor+ hybridomas derived from mice given portal vein donor-specific preimmunization and skin allografts. J Immunol 159:3698-3706.
36. Clark D A, Croitoru K. 2001. TH1/TH2,3 imbalance due to cytokine-producing NK, γδT and NKγδT cells in murine pregnancy decidua in success or failure of pregnancy. Am J Reprod Immunol 45: (in press).
37. Perera P Y, Mayadas T N, Takeuchi O, Akira S, Zaks-Zilberman M, Goyert S M, Vogel S N. 2001. CD11b/CD18 acts in concert with CD14 and toll-like receptor (tlr) 4 to elicit full lipopolysaccharide and taxol-inducible gene expression. J Immunol 166:574-581.
38. Kirschning C J, Wesche H, Merrill Ayres T, Rothe M. 1998. Human toll-like receptor 2 confers responsiveness to bacterial lipopolysaccharide. J Exp Med 188:2091-2097.
39. Dziarski R, Wang Q, Miyake K, Kirschning C J, Gupta D. 2001. MD-2 enables tall-like receptor 2 (tIr2)-mediated responses to lipopolysaccharide and enhances tlr2-mediatd responses to gram-positive and gram-negative bacteria and their cell wall components. J Immunol 166: 1938-1944.
40. Clark D A, Ding J W, Yu G, Levy G A, Gorczynski R M. 2001. Fgl2 prothrombinase in trophoblasts and decidua of aborting normal mouse embryos may be opposed by OX-2. Molec Human Reprod 7:185-194.
41. Poltorak A, He X, Smirnova I, Liu M Y, Van Huffel C, Du X, Birdwell D, Alejos E, Silva M, Galanos C, Freudenberg M, Ricciardi-Castagnoli P, Layton B, Beutler B. 1998. Defective LPS signaling in C3H/HeJ and C57BI/10ScCr mice: mutation in tlr4 gene. Science 282: 2085-2088.

---

The invention claimed is:

1. A method of suppressing an immune response comprising administering an effective amount of an antibody that binds to human MD-1 (SEQ ID NO: 10) or mouse MD-1 (SEQ ID NO: 11) to an animal in need of such treatment, wherein MD-1 is a protein that can regulate expression of RP105.

2. A method according to claim 1 to suppress an immune response to a transplanted organ or tissue.

3. A method according to claim 1 further comprising administering an OX-2 protein or a nucleic acid molecule encoding an OX-2 protein.

* * * * *

SEQUENCE LISTING

```
<160> NUMBER OF SEQ ID NOS: 9

<210> SEQ ID NO 1
<211> LENGTH: 17
<212> TYPE: DNA
<213> ORGANISM: Artificial Sequence
<220> FEATURE:
<223> OTHER INFORMATION: ODN-1

<400> SEQUENCE: 1
agggcagcug cgacacc                                                          17

<210> SEQ ID NO 2
<211> LENGTH: 17
<212> TYPE: DNA
<213> ORGANISM: Artificial Sequence
<220> FEATURE:
<223> OTHER INFORMATION: ODN-2

<400> SEQUENCE: 2 ccugoggaac aucaagu                                                          17

<210> SEQ ID NO 3
<211> LENGTH: 17
<212> TYPE: DNA
<213> ORGANISM: Artificial Sequence
<220> FEATURE:
<223> OTHER INFORMATION: ODN-3

<400> SEQUENCE: 3
agggaccuug ggguccc                                                          17

<210> SEQ ID NO 4
<211> LENGTH: 15
<212> TYPE: PRT
<213> ORGANISM: Murine

<400> SEQUENCE: 4

Leu Val Trp Ile Leu Thr Ser Pro Ser Ser Ser Asp His Gly Ser
```

-continued

```
1               5                   10                  15

<210> SEQ ID NO 5
<211> LENGTH: 15
<212> TYPE: PRT
<213> ORGANISM: Murine

<400> SEQUENCE: 5

Ser Ser Ile Leu Asn Tyr Ser Tyr Pro Leu Cys Glu Glu Asp Gln
1               5                   10                  15

<210> SEQ ID NO 6
<211> LENGTH: 20
<212> TYPE: DNA
<213> ORGANISM: Artificial Sequence
<220> FEATURE:
<223> OTHER INFORMATION: OX-2 riboprobe

<400> SEQUENCE: 6
ccgtcgacca agtggaagtg                                                   20

<210> SEQ ID NO 7
<211> LENGTH: 24
<212> TYPE: DNA
<213> ORGANISM: Artificial Sequence
<220> FEATURE:
<223> OTHER INFORMATION: OX-2 riboprobe

<400> SEQUENCE: 7
acggatcctt gtccagacct gctt                                              24

<210> SEQ ID NO 8
<211> LENGTH: 39
<212> TYPE: DNA
<213> ORGANISM: Artificial Sequence
<220> FEATURE:
<223> OTHER INFORMATION: MD-1 riboprobe

<400> SEQUENCE: 8
atactcgacg ccgccaccat gtgaccatgg cagcgaaaa                              39

<210> SEQ ID NO 9
<211> LENGTH: 27
<212> TYPE: DNA
<213> ORGANISM: Artificial Sequence
<220> FEATURE:
<223> OTHER INFORMATION: MD-1 riboprobe

<400> SEQUENCE: 9
atcggatccc taggtgagtc cagggac                                           27
```